US012629651B2

(12) United States Patent
Su et al.

(10) Patent No.: US 12,629,651 B2
(45) Date of Patent: May 19, 2026

(54) APPARATUS AND PROCESS FOR PREPARING POLYALPHA-OLEFINS

(71) Applicants:CHINA PETROLEUM & CHEMICAL CORPORATION, Beijing (CN); RESEARCH INSTITUTE OF PETROLEUM PROCESSING, SINOPEC, Beijing (CN)

(72) Inventors: Shuo Su, Beijing (CN); Xin Cheng, Beijing (CN); Bing Xu, Beijing (CN); Qinghua Duan, Beijing (CN); Jiayao Yao, Beijing (CN); Zuoxin Huang, Beijing (CN); Xiaojin Tang, Beijing (CN); Tao Huang, Beijing (CN); Ying Han, Beijing (CN)

(73) Assignees: CHINA PETROLEUM & CHEMICAL CORPORATION, Beijing (CN); RESEARCH INSTITUTE OF PETROLEUM PROCESSING, SINOPEC, Beijing (CN)

( * ) Notice: Subject to any disclaimer, the term of this patent is extended or adjusted under 35 U.S.C. 154(b) by 266 days.

(21) Appl. No.: 17/996,751

(22) PCT Filed: Apr. 20, 2021

(86) PCT No.: PCT/CN2021/088301
§ 371 (c)(1),
(2) Date: Oct. 20, 2022

(87) PCT Pub. No.: WO2021/213361
PCT Pub. Date: Oct. 28, 2021

(65) Prior Publication Data
US 2023/0211309 A1 Jul. 6, 2023

(30) Foreign Application Priority Data

Apr. 20, 2020 (CN) ......................... 202010309605.4

(51) Int. Cl.
| | |
|---|---|
| *B01J 19/00* | (2006.01) |
| *C07C 2/06* | (2006.01) |
| *C08F 10/14* | (2006.01) |

(52) U.S. Cl.
CPC ............ *B01J 19/0093* (2013.01); *C07C 2/06* (2013.01); *C08F 10/14* (2013.01);
(Continued)

(58) Field of Classification Search
CPC ............................... B01J 19/0093; C07C 2/06
See application file for complete search history.

(56) References Cited

U.S. PATENT DOCUMENTS

| | | |
|---|---|---|
| 2,997,371 A | 8/1961 | Wadsworth et al. |
| 3,929,749 A | 12/1975 | Cooper et al. |
| | (Continued) | |

FOREIGN PATENT DOCUMENTS

| | | |
|---|---|---|
| CN | 1217726 A | 5/1999 |
| CN | 1289344 A | 3/2001 |
| | (Continued) | |

OTHER PUBLICATIONS

Machine Translation of CN107519835A (Year: 2017).*
Machine Translation of CN-103387628-A (Year: 2013).*
Machine Translation of CN-107586248-A (Year: 2018).*

*Primary Examiner* — Ellen M McAvoy
*Assistant Examiner* — Ming Cheung Po
(74) *Attorney, Agent, or Firm* — NKL Law; Allen Xue

(57) ABSTRACT

An apparatus for preparing polyalpha-olefins includes a mixing unit, a microchannel reaction unit, a high-pressure separation unit, a low-pressure separation unit, a gas circulation unit, a post-treatment unit and a pressure control unit,
(Continued)

the mixing unit, the microchannel reaction unit, the high-pressure separation unit, the low-pressure separation unit that are successively connected. The gas circulation unit, the microchannel reaction unit is provided with the $BF_3$ gas inlet, the mixing unit is provided with the auxiliary feed inlet, and the olefin raw material inlet, the gas circulation unit is connected with the $BF_3$ gas inlet, the low-pressure separation unit is further connected with the post-treatment unit, and the high-pressure separation unit, the pressure control unit, and the gas circulation unit are further successively connected. The apparatus has the advantages of high polymerization reaction speed, high reaction conversion and good product selectivity, and is suitable for large-scale industrial production.

13 Claims, 7 Drawing Sheets

(52) U.S. Cl.
CPC ................ *B01J 2219/00058* (2013.01); *B01J 2219/00065* (2013.01); *B01J 2219/00076* (2013.01)

(56) References Cited

U.S. PATENT DOCUMENTS

| | | | |
|---|---|---|---|
| 4,045,508 A | 8/1977 | Cupples et al. | |
| 4,079,093 A * | 3/1978 | Winter, III | ................ C07C 2/70 585/303 |
| 4,433,197 A | 2/1984 | Vogel et al. | |
| 4,454,366 A | 6/1984 | Vogel et al. | |
| 4,956,512 A * | 9/1990 | Nissfolk | .............. C10M 107/02 585/521 |
| 5,846,429 A | 12/1998 | Shimizu et al. | |
| 6,939,943 B2 | 9/2005 | Wettling et al. | |
| 7,772,335 B1 | 8/2010 | Cao et al. | |
| 8,747,656 B2 * | 6/2014 | Tonkovich | ............. C10G 45/02 208/209 |
| 10,815,165 B1 * | 10/2020 | Agee | ........................ C10G 9/00 |
| 2006/0178545 A1 | 8/2006 | Yang et al. | |
| 2007/0256736 A1 * | 11/2007 | Tonkovich | .............. A61P 17/00 137/92 |

FOREIGN PATENT DOCUMENTS

| | | | | |
|---|---|---|---|---|
| CN | 103387628 A | * | 11/2013 | |
| CN | 104370675 B | | 12/2015 | |
| CN | 105152834 A | | 12/2015 | |
| CN | 107488242 A | | 12/2017 | |
| CN | 107519835 A | * | 12/2017 | .............. B01J 4/002 |
| CN | 107586248 A | * | 1/2018 | |
| CN | 108431050 A | | 8/2018 | |
| CN | 108728151 A | | 11/2018 | |
| CN | 109293858 A | | 2/2019 | |
| CN | 109593591 A | | 4/2019 | |
| CN | 208975763 U | | 6/2019 | |
| CN | 111013511 A | | 4/2020 | |
| JP | 2009256217 A | | 11/2009 | |
| RU | 2494113 C2 | | 9/2013 | |
| RU | 2666736 C1 | | 9/2018 | |

* cited by examiner

APPARATUS AND PROCESS FOR PREPARING POLYALPHA-OLEFINS

TECHNICAL FIELD

The present invention relates to an apparatus and a process for preparing polyalpha-olefins, in particular to an apparatus and a process for preparing polyalpha-olefins by using a continuous process.

BACKGROUND TECHNOLOGY

Polyalpha-olefins are usually obtained by polymerizing one or more linear alpha-olefins through oligomerization reaction under the action of catalysts. The hydrogenated polyalpha-olefins obtained by separation and hydrogenation of polyalpha-olefins can be used for blending into high-quality synthetic base oils. Polyalpha-olefin synthetic base oils, also known as PAO synthetic base oils, have excellent properties such as high viscosity index, ultra-low pour point, excellent thermal and oxidative stability, and high flash point, so it has comprehensive uses. PAO synthetic base oils are classified according to their kinematic viscosities at 100° C. The mainstream products include PAO4, PAO6, PAO8, PAO10, PAO40, PAO100, and the like. Among them, the low-viscosity PAOs with a kinematic viscosity at 100° C. between 4 and 8 cSt are most widely used, mainly for blending into various types of high-grade engine oils. The use of low-viscosity PAOs can reduce engine cold torque loss while extending drain intervals and improving fuel economy.

The conventional process for preparing polyalpha-olefins usually uses a Lewis acid catalyst system to allow alpha-olefins to undergo the oligomerization reaction, and poly-mers with different degrees of polymerization will be formed during the reaction. At present, the catalysts used in the production of low-viscosity poly-alpha-olefins in the industry are mainly $BF_3$-auxiliary catalysts. Batch or con-tinuous stirred tank reactors are used in typical production processes. In the oligomerization reaction system in which alpha-olefins are catalyzed by $BF_3$-auxiliary, $BF_3$ in the gas phase needs to be fully dispersed and mixed with auxiliary and alpha-olefins in the liquid phase, a part thereof dissolves to form an active cationic catalyst and then initiates the alpha-olefin oligomerization reaction. $BF_3$ dissolution and interphase mass transfer determine the macroscopic reaction rate, the conversion, and the like. In addition, if the reaction time is too short, the olefin conversion tends to be low and the product yield is not high. If the reaction time is too long, the formed alpha-olefin oligomer may undergo side reac-tions such as a secondary polymerization reaction that increases the degree of polymerization and an isomerization reaction that causes a decrease in the viscosity index.

U.S. Pat. No. 4,045,508A discloses a method for the continuous preparation of polyalpha-olefins, which is char-acterized by combining a stirred reactor and a tubular reactor to control a multi-step polymerization process. However, this process leads to more secondary polymerization reac-tion of oligomers, and the content of trimers is greatly reduced.

CN104370675B discloses a process for preparing poly-alpha-olefins in a continuous manner, the process introduces alpha-olefins into a glassy microchannel continuous reactor in a continuous manner, and conducts a polymerization reaction in the presence of an aluminum compound catalyst and an auxiliary agent to produce polyalpha-olefins. This process consumes a large amount of catalyst and requires a higher reaction temperature.

On the other hand, after the reaction is carried out by using boron trifluoride or its complex as a catalyst, it is often necessary to remove boron trifluoride or its complex from the product. For this reason, a method of neutralizing with alkaline substances such as aqueous sodium hydroxide solu-tion and ammonia water and then water washing is usually used. However, this method will cause serious environmen-tal pollution problems, and the catalyst cannot be recycled. The produced waste alkali liquor and fluorine-containing wastewater and boron-containing wastewater are very dif-ficult to treat. At the same time, the water washing process will cause a lot of waste of water resources. In addition, with the tightening of national environmental protection policies, a large number of polluting enterprises have been shut down, and projects without proper pollution disposal methods cannot be implemented.

So far, a variety of boron trifluoride removal and recovery methods have been proposed, but all have various limita-tions.

U.S. Pat. No. 4,433,197A discloses a method of using SiO2 particles to adsorb $BF_3$ in a polymerization reaction solution at a lower temperature, and then regenerating $BF_3$ by a method of heating at a low-pressure. U.S. Pat. No. 2,997,371A precipitates polyacrylonitrile on the surface of inert particles such as activated carbon and activated alu-mina, and then uses it to adsorb $BF_3$; U.S. Pat. No. 5,846,429A discloses the use of polyacrylonitrile fibers to adsorb $BF_3$, and using the heating after the adsorption is saturated to release $BF_3$. Chinese patent application CN1289344A discloses a method for utilizing metal fluoride to separate and recover $BF_3$. First, metal fluoride and $BF_3$ undergo chemical reaction to generate tetrafluoroborate to realize $BF_3$ separation, and then tetrafluoroborate is decomposed under a high temperature heating condition to release $BF_3$. U.S. Pat. No. 4,454,366A introduced a method of using polyvinyl alcohol and $BF_3$ to form a stable complex to remove $BF_3$.

U.S. Pat. No. 6,939,943B2 discloses a method for recov-ering $BF_3$ by using methanol and ethanol, wherein, at low temperature, methanol or ethanol is added to the polymer-ization reaction solution, and $BF_3$ is extracted into the alcohol phase to separate $BF_3$.

Chinese patent application CN1217726A discloses a separation method of electroprecipitation, which applies an electric field to the polymerization solution to separate the boron trifluoride complex from the polymerization product.

Taking advantage of the instability of the boron trifluoride complex, U.S. Pat. No. 3,929,749A adopts a heating method to thermally crack the complex in the polymerization solu-tion, and the $BF_3$ gas overflows to realize the separation of the catalyst.

In the reaction using boron trifluoride as one of the catalyst components, it is the complex formed by boron trifluoride and the ligand to play a catalytic role. These boron trifluoride complexes are usually selected for a specific ligand, and the molar ratio between boron trifluoride and the ligand is also specific. Therefore, if the catalyst is to be recycled and reused, it needs to be carried out without changing the coordination situation between boron trifluo-ride and the ligand, because if the coordination situation changes, the catalytic activity of the catalyst will be weak-ened, or the catalyst will be even deactivated.

However, whether it is the adsorption method using the complexation of $BF_3$ with the adsorbent, the extraction method using the rule of the likes dissolving each other, the electroprecipitation method using an electric field, or the thermal cracking method, there are more or less various problems, such as unfavorable factors such as poor separation efficiency, destruction of catalyst structure, and large influence of side reactions limit its application in industrial scale-up production.

Furthermore, the batch stirred tank type reaction process reported in the prior art has the defects of large volume of the stirred tank reactor, large occupied area, very strict requirements on the control of process parameters, complex process operation, long reaction time and production period and the like, and although the batch stability can be ensured, the continuous tank type preparation process cannot realize ideal conversion and selectivity, and the two processes cannot well treat the catalyst in the product. Therefore, there is a need in the art for an apparatus and method for preparing alpha-olefin oligomers, which is high in conversion, high in selectivity, simple in process, low in investment cost, and safe and environmentally friendly.

It is noted that the information disclosed in the foregoing background section is only for enhancing the understanding of the background of the present invention and therefore it may contain information that does not form the prior art that is already known to a person of ordinary skill in the art.

SUMMARY OF THE INVENTION

The present invention provides an apparatus and process for preparing polyalpha-olefins.

Specifically, the present invention comprises to the following aspects.

In the first aspect, the present invention provides an apparatus for preparing polyalpha-olefins.

The apparatus for preparing polyalpha-olefins of the present invention comprises a mixing unit 1, a microchannel reaction unit 2, a high-pressure separation unit 3, a low-pressure separation unit 4, a gas circulation unit 5, a post-treatment unit 6 and a pressure control unit 7, the mixing unit 1, the microchannel reaction unit 2, the high-pressure separation unit 3, the low-pressure separation unit 4, and the gas circulation unit 5 are successively connected, the microchannel reaction unit 2 is provided with the $BF_3$ gas inlet 01, the mixing unit 1 is provided with the auxiliary feed inlet 02, and the olefin raw material inlet 03, the gas circulation unit 5 is connected with the $BF_3$ gas inlet 01, the low-pressure separation unit 4 is further connected with the post-treatment unit 6, and the high-pressure separation unit 3, the pressure control unit 7, and the gas circulation unit 5 are further successively connected. Preferably, the mixing unit 1 is further provided with a $BF_3$ gas inlet. Optionally, the gas circulation unit 5 is connected with the $BF_3$ gas inlet provided with the mixing unit 1. Optionally, the post-treatment unit 6 is connected with the mixing unit 1 to recycle a complex of auxiliary feed with $BF_3$ and an unreacted olefin raw material.

According to the apparatus of the present invention, the mixing unit 1 is capable of uniformly mixing the stream entering therein (the mixing unit 1 is preferably a mixer, more preferably a static mixer and/or a dynamic mixer). The stream entering the mixing unit 1 comprises an auxiliary feed and an olefin raw material, and optionally a recycled complex of auxiliary feed and $BF_3$, and an unreacted olefin raw material. Preferably, the stream entering the mixing unit 1 may also include a $BF_3$ gas, so that the auxiliary feed, the olefin raw material and the $BF_3$ gas can be mixed in the mixing unit. Optionally, the structure and parameter of the mixer are: the working temperature is 20-200° C., and the upper limit of the working pressure is not more than 20 MPa; the mixer is preferably a static mixer, more preferably a static mixer with enhanced mixing; the number of the mixer(s) can be one or more. When two or more mixers are used, these mixers can be connected in parallel, in series, or both in parallel and in series. The mixer may optionally have a heat exchange layer. The mixer may optionally have a filler; the filler in the mixer may be selected from Pall ring, ceramic ball, regular filler, corrugated filler, wire mesh or plastic ring. In case that the stream entering the mixing unit 1 includes the $BF_3$ gas, the mixing unit 1 comprises a first mixer for mixing any two of the auxiliary feed, the olefin raw material and the $BF_3$ gas, and a second mixer for further mixing the mixture with the third one; more preferably, the mixing unit 1 comprises a first mixer for mixing one of the olefin raw material and the $BF_3$ gas, and the auxiliary feed, and a second mixer for further mixing the mixture with the other of the olefin raw material and the $BF_3$ gas. For example, the mixing unit 1 comprises a first mixer for mixing the olefin raw material with the auxiliary feed, and a second mixer for mixing the mixture with the $BF_3$ gas; or the mixing unit 1 comprises a first mixer for mixing the $BF_3$ gas with the auxiliary feed, and a second mixer for mixing the mixture with the olefin raw material; or the mixing unit 1 comprises a mixer for mixing the $BF_3$ gas, the auxiliary feed and the olefin raw material concurrently.

The microchannel reaction unit 2 enables the microchannel reaction of a $BF_3$ gas from the $BF_3$ gas inlet 01, and a mixed stream of an auxiliary feed and an olefin raw material as well as an optional $BF_3$ gas from the mixing unit 1 therein, preferably, the microchannel reaction unit 2 enables the microchannel reaction of a $BF_3$ gas from the $BF_3$ gas inlet 01, and a mixed stream of an auxiliary feed, an olefin raw material and a $BF_3$ gas from the mixing unit 1 therein. Preferably, the microchannel reaction unit is a microchannel reactor. The number of the microchannel reactor(s) may be one or more, preferably one, two, three, four, five or six. When two or more microchannel reactors are used, these microchannel reactors can be connected in series, in parallel, or both in parallel and in series.

The high-pressure separation unit 3 enables an intermediate stream entering therein to perform a gas liquid separation, the separated gas phase enters the gas circulation unit 5 via the pressure control unit 7, and the separated liquid phase enters the low-pressure separation unit 4. The high-pressure separation unit 3 is preferably a high-pressure separator. The number of the high-pressure separator(s) may be one or more, preferably one, two, three, four, five or six. When two or more high-pressure separators are used, these high-pressure separators can be connected in series, in parallel, or both in parallel and in series.

The low-pressure separation unit 4 enables an intermediate stream entering therein to perform a gas liquid separation, the separated gas phase enters the gas circulation unit 5, and the separated liquid phase enters the post-treatment unit 6. The low-pressure separation unit 4 is preferably a low-pressure separator. The number of the low-pressure separator(s) may be one or more, preferably one, two, three, four, five or six. When two or more low-pressure separators are used, these low-pressure separators can be connected in series, in parallel, or both in parallel and in series.

The gas circulation unit 5 enables the recovery of the $BF_3$ gas entering therein and the delivery of the recovered $BF_3$ gas via the $BF_3$ gas inlet 01 to the microchannel reaction unit 2 for the recycled use. The gas circulation unit 5 can be one or more of compressor, gas circulation pump and vacuum pump. The number of compressor(s), gas circulation pump (s) and vacuum pump(s) may be one or more, so that the gas circulation unit can realize one-stage circulation or multi-stage circulation. Optionally, the gas circulation unit 5 is connected with the $BF_3$ gas inlet provided with the mixing unit 1 to deliver the recovered $BF_3$ gas to the mixing unit for mixing with the auxiliary feed and the olefin raw material.

The post-treatment unit 6 enables the post-treatment of the stream entering therein to produce a polyolefin product. The post-treatment unit can be one or more of an adsorption device, an extraction device, a distilling device, a centrifugation device, a sedimentation device, an alkaline washing device and a water washing device. Preferably, the post-treatment unit 6 is a sedimentation device or a centrifugation device. The sedimentation device or centrifugation device enables the separation of the stream entering therein into a light liquid phase and a heavy liquid phase, the heavy liquid phase is the complex of auxiliary feed and $BF_3$ and the unreacted olefin raw material, and optionally returned to the mixing unit 1 to continue the participation in the continuous reaction. The light liquid phase is a crude polyolefin product, which can be subjected to a further post-treatment.

The pressure control unit can control the pressures of the microchannel reaction unit 2 and the high-pressure separation unit 3 to promote the smooth progress of the microchannel reaction and the smooth progress of the gas-liquid separation of the stream in the high-pressure separation unit 3. The pressure control unit 7 can be one or more of a back pressure valve, a throttle valve and a pressure reducing valve. Optionally, the pressure control unit 7 can each independently control the working pressure of the microchannel reaction unit 2 and the working pressure of high-pressure separation unit 3. Optionally, the pressure control unit 7 can control the working pressure of the microchannel reaction unit 2 to be identical to the working pressure of the high-pressure separation unit 3.

According to the apparatus of the present invention, preferably, a gas purification unit 8 is provided between the low-pressure separation unit 4 and the gas circulation unit 5, and/or, a gas purification unit 8 is provided between the pressure control unit 7 and the gas circulation unit 5. The gas purification unit 8 enables drying and/or purifying the $BF_3$ gas entering therein. The gas purification unit 8 can be one or more of a gas filter, an adsorption dryer, a freeze dryer and a cyclone separator, preferably an adsorption dryer, in which a filler can be filled up, and the filler can be one or more of silica gel, anhydrous calcium sulfate, anhydrous calcium chloride, and active carbon.

According to the apparatus of the present invention, optionally, the microchannel reaction unit 2 is one microchannel reactor or the combination of two or more microchannel reactors. The structure and parameter of the microchannel reactor is as follows: the reaction channel is 2-10000 channels in parallel, the working temperature range is -70 to 300° C., the allowable maximum reaction pressure does not exceed 20 MPa, the allowable maximum heat transfer medium pressure does not exceed 10 MPa; the fluid channel volume without mixing inserts is 0.1-20000 L, the volume flow rate is 1-50000 L/h. Further preferably, the reaction channel is 2-5000 channels, more preferably 2-500 channels. For example, the reaction channel can be of 2, 3, 4, 5, 6, 7, 8, 9, 10, 11, 12, 13, 14, 15, 16, 17, 18, 19, 20, 21, 22 channels or the like. In the microchannel reactor of the present invention, each reaction channel can have a cross-sectional area of 1 $mm^2$ to 150 $mm^2$, and a length of 50 mm to 5000 mm. Preferably, a mixing member that can promote the mixing of the reaction streams is provided in each reaction channel, and the mixing member is a member well known in the art that can promote the mixing of the reaction streams and enhance the turbulence, and it can be a mixing disk, and a first mixing member and a second mixing member according to the present invention. Preferably, the microchannel reactor of the present invention is provided with a header pipe for introducing the reaction gas and branch pipes for distributing the reaction gas to each reaction channel.

According to the apparatus of the present invention, a preferred microchannel reactor (hereinafter sometimes also referred to as the preferred microchannel reactor of the present invention) includes: a shell 003; a feeding zone 023, a mixing zone 008, a reaction zone 009, and a collection zone 024 are successively arranged and communicated along a first direction in the shell 003, wherein the shell 003 is provided with a feed pipe 002 communicated with the feeding zone 023 and a discharge pipe 001 communicated with the collection zone 024, and the mixing zone 008 is provided with a mixing channel 014 extending along the first direction;

a fluid distribution pipe 017, the fluid distribution pipe 017 is extended from the exterior of the shell 003 into the mixing channel 014, the fluid distribution pipe 017 is connected with a fluid distributor 016 at an end of the mixing channel 014;

the feed pipe 002 is connected to the mixing unit 1, and can be used to input the mixture of the olefin raw material and the auxiliary feed, the fluid distribution pipe 017 is connected to the $BF_3$ gas inlet 01, and can be used to input the $BF_3$ gas, and the discharge pipe 001 is connected to the high-pressure separation unit 3.

In the present invention, the first direction is the flow direction of the stream, and it may be a horizontal direction, an elevation direction, or the like. The elevation direction is preferred, and the elevation direction from bottom to top is more preferred.

In the present invention, the mixing zone 008 and the feeding zone 023 can be partitioned by a first partition plate 019. The first partition plate 019 is provided with a plurality of through holes, and each through hole is aligned with the mixing channel 014, so that the mixing zone 008 is communicated with the feeding zone 023.

According to the apparatus of the present invention, in the preferred microchannel reactor:

In one embodiment of the present invention, the fluid distributor 016 is at least one selected from powder sintered body with micropores, mesoporous foam material, wire mesh, and tube with microslits or micropores.

Preferably, the fluid distributor is a cylindrical powder sintered body with micropores.

In one embodiment of the present invention, the fluid distributor 016 has a cross-sectional area of 0.01 cm2-200 cm2, and a length of 1 mm-2000 mm. The mixing channel has a circular cross-section; preferably, the mixing channel has a cross-sectional area of 0.05 cm2-400 cm2, and a length of 50 mm-5000 mm. In the present invention, the length and the cross-sectional area of the mixing channel 014 are both greater than the length and the cross-sectional area of the fluid distributor 016.

In one embodiment of the present invention, the mixing zone is provided with 1-100 (preferably 1-50, more preferably 2-10) mixing channels, the fluid distribution pipe 017 includes a main pipe extending from the exterior of the shell into the feeding zone and branch pipes extending from the feeding zone into each mixing channel 014 with fluid distributors 016 connected to branch pipe ends.

In one embodiment of the present invention, in the mixing channel 014, a first mixing member 015 is disposed downstream of the fluid distributor 016.

In one embodiment of the present invention, the first mixing member 015 is provided with a main flow portion and a branch flow portion that are alternately arranged and communicated along the first direction, the main flow portion is provided with a single main flow passage, and the branch flow portion is provided with a plurality of branch flow passages. A collection cavity communicated with a plurality of branch flow passages is disposed downstream of the branch flow portion. The first mixing member can be formed by splicing a plurality of plate members (the number can be 2-100, preferably 2-50, more preferably 10-30) (the thickness is about 0.2 mm-10 mm) arranged along a first direction, and the structures such as holes and cavities that correspond to the main flow passage 0001, the branch flow passage 0002 and the collection cavity 0003 are formed on each plate member, which is convenient for processing and manufacturing.

In one embodiment of the present invention, the mixing zone can comprise a first heat exchange cavity 013 disposed in the shell, the mixing channel is disposed in the first heat exchange cavity, the shell is provided with a first heat exchange medium inlet 004 and a first heat exchange medium outlet 005 that are communicated with the first heat exchange cavity.

In one embodiment of the present invention, the volumetric ratio of the first heat exchange cavity to the mixing channel is 2-50; preferably, the volumetric ratio of the first heat exchange cavity to the mixing channel is 5-30. In the mixing zone 008, the mixing channel 014 and the first heat exchange cavity 013 are isolated from each other and not communicated with each other, but the heat conduction can be achieved between each other, and pipe fittings with good thermal conductivity can be used in the mixing channel 014.

In one embodiment of the present invention, a transition zone 020 is provided between the mixing zone and the reaction zone, the transition zone is provided with a stabilization channel 021 with constant cross-section and a diffusion channel 022 with gradually enlarged cross-section arranged and communicated along the first direction, the stabilization channel is communicated with the mixing channel, the diffusion channel is communicated with the reaction zone.

In one embodiment of the present invention, a discharge pipe 018 extending to the exterior of the shell is connected to the stabilization channel.

In one embodiment of the present invention, the diffusion channel is provided with a diffusion plate with meshes or slits.

In one embodiment of the present invention, the two ends of the transition zone 020 are respectively provided with partition plates with through holes, so as to be respectively isolated from the mixing zone 008 (mainly the first heat exchange cavity 013) and the reaction zone 009 (mainly the second heat exchange cavity 012), and connected to each mixing channel 014 and each reaction channel 010 through each through hole on each partition plate respectively, and the diffusion channel 022 and the stabilization channel 021 can be pipe fittings provided between two partition plates.

In one embodiment of the present invention, the reaction zone is provided with a plurality of parallel reaction channels extending along the first direction and communicated with the mixing channel via the stabilization channel 021 and the diffusion channel 022. The reaction channel has a cross section in at least one of circular, rectangular and triangular shapes. The number of reaction channels is, for example, 2-10000 channels, preferably 2-5000 channels, and more preferably 2-500 channels.

In one embodiment of the present invention, the reaction channel is provided with a second mixing member, and the second mixing member includes a base strip extending along the first direction and a tooth element connected to the base strip and extended transversely to the base strip; the tooth element is of at least one of triangular, arcual, wavy, and spiral shapes. Preferably, the tooth element is of triangular shape, and on one side of the triangle adjacent to the base strip, one corner is connected to the base strip, and the other corner is 0.01 mm-20 mm away from the base strip.

In one embodiment of the present invention, each of reaction channels is each independently provided with a plurality of the second mixing members (the number can be 2-100, preferably 2-50, more preferably 10-30), which are stacked at intervals, and the tooth elements of the second mixing member are staggered with each other.

Preferably, the cross-section of the reaction channel is rectangular, and the tooth elements extend between a set of opposite sides of the rectangle.

In one embodiment of the present invention, the reaction channel has a cross-sectional area of $1 \text{ mm}^2$–$150 \text{ mm}^2$, and a length of 50 mm-5000 mm, the minimum distance between the reaction channels is 1 mm-50 mm, and the second mixing member has a thickness of 0.1 mm-3 mm, and the spacing between adjacent tooth elements is 1 mm-50 mm, preferably, the reaction channel has a length of 100 mm-3000 mm, and a minimum spacing between the reaction channels of 3 mm-30 mm, the second mixing member has a thickness of 0.2 mm-2 mm, and the spacing between adjacent tooth elements is 1.5 mm-20 mm.

In one embodiment of the present invention, the reaction zone can be provided with a second heat exchange cavity 012 disposed in the shell, the reaction channel is disposed in the second heat exchange cavity, the shell is provided with a second heat exchange medium inlet 006 and a second heat exchange medium outlet 007 that are communicated with the second heat exchange cavity.

In one embodiment of the present invention, the volumetric ratio of the second heat exchange cavity to the reaction channel is 2-50; preferably, the volumetric ratio of the second heat exchange cavity to the reaction channel is 5-30.

In one embodiment of the present invention, the second heat exchange cavity 012 may be mainly formed by the shell 003, and at two ends are respectively the second partition plate 025 between the reaction zone 009 and the collection zone 024 and the partition plate between the reaction zone 009 and the transition zone 020.

The apparatus for preparing polyalpha-olefins of the present invention can be used for synthesizing polyalpha-olefin synthetic oil by a continuous method, and has the advantages of high reaction speed, high reaction conversion and good product selectivity.

The apparatus for preparing polyalpha-olefins using the preferred microchannel reactor of the present invention can realize continuous and efficient mixing of the reaction system, maintain the fluid to flow in a plug flow-like manner, ensure the consistency of the residence time of the reaction fluid as much as possible, and avoid the undesirable product selectivity due to residence time distribution.

In a second aspect, the present invention provides a process for preparing polyalpha-olefins.

The process for preparing polyalpha-olefins of the present invention comprises: a mixed stream obtained after mixing an olefin raw material and an auxiliary feed in a mixing unit and a $BF_3$ gas are each independently allowed to enter a microchannel reaction unit, an intermediate stream formed after the polymerization reaction in the microchannel reaction unit is allowed to enter a high-pressure separation unit, the intermediate material undergoes a first gas-liquid separation in the high-pressure separation unit, the separated liquid phase enters a low-pressure separation unit, a second gas-liquid separation occurs in the low-pressure separation unit, the liquid phase separated from the low-pressure separation unit enters a post-treatment unit, and a polyolefin product is obtained after the treatment in the post-treatment unit; The gas phases separated from the high-pressure separation unit and the low-pressure separation unit ($BF_3$ gas) enter a gas circulation unit, and the $BF_3$ gas is recovered for the recycled use. Preferably, the $BF_3$ gas is further fed into the mixing unit, so that the $BF_3$ gas, the olefin raw material and the auxiliary feed are mixed in the mixing unit, and then the mixed stream and the $BF_3$ gas each independently enter the microchannel reaction unit. Optionally, the heavy liquid phase containing the complex of the auxiliary feed and $BF_3$ and the unreacted olefin raw material obtained after the treatment in the post-treatment unit is recycled to the mixing unit.

In one embodiment of the present invention, in the case of feeding the $BF_3$ gas to the mixing unit, the order of mixing the $BF_3$ gas, the olefin raw material and the auxiliary feed is not particularly limited, and the mixing manner can be as follows: any two of the $BF_3$ gas, the olefin raw material and the auxiliary feed can be mixed, and then mixed with the third one, or the $BF_3$ gas, the olefin raw material and the auxiliary feed can be mixed concurrently. For example, the $BF_3$ gas and the auxiliary feed can be mixed to form a complex, and then mixed with the olefin raw material, or the auxiliary feed and the olefin raw material can be mixed, and then mixed with the $BF_3$ gas, or the $BF_3$ gas, the olefin raw material and the auxiliary feed can be mixed concurrently.

In one embodiment of the present invention, the olefin in the olefin raw material is one or more of $C_3$-$C_{20}$ alpha-olefins, preferably one or more of $C_5$-$C_{15}$ alpha-olefins, more preferably one or more of $C_7$-$C_{14}$ alpha-olefins. For example, it can be the olefins commonly used in the preparation of PAO synthetic base oils, such as nonene and decene.

In one embodiment of the present invention, the olefin raw material can further contain $C_5$-$C_{20}$ alkane and/or $C_1$-$C_{20}$ oxygen-containing compound as solvent. Relative to the total mass of the olefin raw material, the mass fraction of the $C_5$-$C_{20}$ alkane can be 0-80%, preferably 0.5-50%, most preferably 1-30%. Relative to the total mass of the olefin raw material, the mass fraction of the $C_1$-$C_{20}$ oxygen-containing compound can be 0-20%, preferably 0-10%, most preferably 0.001-5%. The $C_5$-$C_{20}$ alkane can be one or more of n-alkane, iso-alkane and cycloalkane; the $C_1$-$C_{20}$ oxygen-containing compound can be one or more of n-alkanol, iso-alcohol and ketone. A Fischer-Tropsch olefin raw material can be used as the mixture of $C_3$-$C_{20}$ alpha-olefin, $C_5$-$C_{20}$ alkane, and $C_1$-$C_{20}$ oxygen-containing compound (namely the olefin raw material).

In one embodiment of the present invention, the auxiliary feed can be a commonly used auxiliary agent that can be used as an electron donor of $BF_3$, and can be one or more of an alcohol having a carbon atom number of 1-20, an ether having a carbon atom number of 1-20, an aldehyde having a carbon atom number of 1-20, a ketone having a carbon atom number of 1-20, an ester having a carbon atom number of 1-30, a carboxylic acid having a carbon atom number of 1-20 and a phenol having a carbon atom number of 1-20, preferably an alcohol having a carbon atom number of 1-10, more preferably an alcohol having a carbon atom number of 3-5, for example, one or more of n-propanol, iso-propanol, n-butanol, iso-butanol, n-pentanol and iso-pentanol.

According to the process of the present invention, the mixing unit is capable of uniformly mixing the stream entering therein, and is preferably a mixer, more preferably a static mixer and/or a dynamic mixer. The stream entering the mixing unit comprises an auxiliary feed and an olefin raw material, and optionally a recycled complex of auxiliary feed and $BF_3$, and an unreacted olefin raw material. Preferably, the stream entering the mixing unit may also include a $BF_3$ gas, so that the auxiliary feed, the olefin raw material and the $BF_3$ gas can be mixed in the mixing unit. Herein, as stated above, the order of mixing the $BF_3$ gas, the olefin raw material and the auxiliary feed in the mixing unit is not particularly limited. The mixing unit is preferably a mixer, and the structure and parameter of the mixer is preferably as follows: the working temperature is 20-200° C., and the upper limit of the working pressure is not more than 20 MPa; the mixer is preferably a static mixer, more preferably a static mixer with enhanced mixing. The number of the mixer(s) can be one or more. When two or more mixers are used, these mixers can be connected in parallel, in series, or both in parallel and in series. The mixer may optionally have a heat exchange layer. The mixer may optionally have a filler.

The filler in the mixer may be selected from Pall ring, ceramic ball, regular filler, corrugated filler, wire mesh or plastic ring. In case that the stream entering the mixing unit includes the $BF_3$ gas, the mixing unit comprises a mixer for mixing any two of the auxiliary feed, the olefin raw material and the $BF_3$ gas, and a mixer for further mixing the mixture with the third one; more preferably, the mixing unit comprises a mixer for mixing one of the olefin raw material and the $BF_3$ gas, and the auxiliary feed, and a mixer for further mixing the mixture with the other of the olefin raw material and the $BF_3$ gas. For example, the mixing unit comprises a mixer for mixing the olefin raw material and the auxiliary feed, and a mixer for mixing the mixture and the $BF_3$ gas; or the mixing unit 1 comprises a mixer for mixing the $BF_3$ gas and the auxiliary feed, and a mixer for mixing the mixture and the olefin raw material; or the mixing unit comprises a mixer for mixing the $BF_3$ gas, the auxiliary feed and the olefin raw material concurrently.

The microchannel reaction unit enables the microchannel reaction of a mixed stream of a $BF_3$ gas, an auxiliary feed and an olefin raw material therein. Preferably, the microchannel reaction unit enables the microchannel reaction of a $BF_3$ gas from the $BF_3$ gas inlet, and a mixed stream of an auxiliary feed, an olefin raw material and an optional $BF_3$ gas from the mixing unit therein. Preferably, the microchannel reaction unit is a microchannel reactor. The number of the microchannel reactor(s) may be one or more, preferably one, two, three, four, five or six. When two or more microchannel reactors are used, these microchannel reactors can be connected in series, in parallel, or both in parallel and in series. Any of microchannel reactors as described in the above first aspect can be used in the microchannel reaction unit. The structure and parameter of the microchannel reactor is preferably as follows: the reaction channel is 2-10000 channels in parallel, the working temperature range is-70 to 300° C., the allowable maximum reaction pressure does not exceed 20 MPa, the allowable maximum heat transfer medium pressure does not exceed 10 MPa; the fluid channel volume without mixing inserts is 0.001-20000 L, and the volume flow rate is 1-5000 L/h. Further preferably, the reaction channel is 2-5000 channels, more preferably 2-500 channels. For example, the reaction channel can be of 2, 3, 4, 5, 6, 7, 8, 9, 10, 11, 12, 13, 14, 15, 16, 17, 18, 19, 20, 21, 22 channels or the like. In the microchannel reactor of the present invention, each reaction channel can have a cross-sectional area of 1 mm$^2$ to 150 mm$^2$, and a length of 50 mm to 5000 mm. Preferably, a mixing member that can promote the mixing of the reaction streams is provided in each reaction channel, and the mixing member is a member well known in the art that can promote the mixing of the reaction streams and enhance the turbulence, and it can be a mixing disk, and a first mixing member and a second mixing member according to the present invention. Preferably, the microchannel reactor of the present invention is provided with a header pipe for introducing the reaction gas and branch pipes for distributing the reaction gas to each reaction channel.

The high-pressure separation unit enables an intermediate stream entering therein to perform a gas liquid separation, the separated gas phase enters the gas circulation unit via the pressure control unit, and the separated liquid phase enters the low-pressure separation unit. The high-pressure separation unit is preferably a high-pressure separator. The number of the high-pressure separator(s) may be one or more, preferably one, two, three, four, five or six. When two or more high-pressure separators are used, these high-pressure separators can be connected in series, in parallel, or both in parallel and in series.

The low-pressure separation unit enables an intermediate stream entering therein to perform a gas liquid separation, the separated gas phase enters the gas circulation unit, and the separated liquid phase enters the post-treatment unit. The low-pressure separation unit is preferably a low-pressure separator. The number of the low-pressure separator(s) may be one or more, preferably one, two, three, four, five or six. When two or more low-pressure separators are used, these low-pressure separators can be connected in series, in parallel, or both in parallel and in series.

The gas circulation unit enables the recovery of the BF$_3$ gas entering therein and the delivery of the recovered BF$_3$ gas to the microchannel reaction unit for the recycled use. The gas circulation unit can be one or more of compressor, gas circulation pump and vacuum pump. The number of compressor(s), gas circulation pump(s) and vacuum pump(s) may be one or more, so that the gas circulation unit can realize one-stage circulation or multi-stage circulation. Optionally, the gas circulation unit delivers the recovered BF$_3$ gas to the mixing unit to be mixed with the auxiliary feed and the olefin raw material.

The post-treatment unit enables the post-treatment of the stream entering therein to produce a polyolefin product. The post-treatment unit is preferably one or more of adsorption device, extraction device, distilling device, centrifugation device, sedimentation device, alkaline washing device and water washing device. Preferably, the heavy liquid phase containing the complex of auxiliary feed and BF$_3$ and the unreacted olefin raw material obtained from the post-treatment unit is returned to the mixing unit to continue to the participation in the continuous reaction.

The pressure control unit can control the pressures of the microchannel reaction unit and the high-pressure separation unit to promote the smooth progress of the microchannel reaction and the smooth progress of the gas-liquid separation of the streams in the high-pressure separation unit. The pressure control unit can be one or more of a back pressure valve, a throttle valve and a pressure reducing valve. Optionally, the pressure control unit can each independently control the working pressure of the microchannel reaction unit and the working pressure of the high-pressure separation unit. Optionally, the pressure control unit can control the working pressure of the microchannel reaction unit to be identical to the working pressure of the high-pressure separation unit.

In one embodiment of the present invention, according to the process of the present invention, the speed for the olefin raw material entering the mixing unit is 10-5000 L/h, preferably 20-4000 L/h, more preferably 40-2500 L/h. The speed for the auxiliary feed entering the mixing unit is 0.01-1000 L/h, preferably 0.1-800 L/h, more preferably 0.2-500 L/h. The gas-entering speed for the BF$_3$ gas entering the microchannel reaction unit (including the initially injected BF$_3$ gas and the optionally recycled BF$_3$ gas) is 5-200000 L/h, preferably 50-100000 L/h, more preferably 100-50000 L/h. Generally speaking, the gas-entering speed for the BF$_3$ gas entering the microchannel reaction unit is controlled to be a constant value or within a numerical range, and the amount of the initially injected BF$_3$ gas can be adjusted according to the amount of the recycled BF$_3$ gas, as long as the total amount of the two is the constant value or within the numerical range. In the case of further feeding the BF$_3$ gas to the mixing unit, the speed for the BF$_3$ gas entering the mixing unit is 4-180000 L/h, preferably 45-90000 L/h, more preferably 90-45000 L/h.

In one embodiment of the present invention, according to the process of the present invention, preferably, the reaction temperature in the microchannel reaction unit is 0-120° C., preferably 10-80° C., more preferably 20-60° C. The reaction pressure in the microchannel reaction unit is 0.01-10 MPa, preferably 0.01-8 MPa, more preferably 0.1-6 MPa. The residence time of the olefin raw material in the microchannel reaction unit is 1-3600 seconds, preferably 10-1800 seconds, more preferably 15-1000 seconds. In the microchannel reaction unit, the mass ratio of the auxiliary feed:the olefin raw material:the total amount of BF$_3$ gas is 1:1-1000: 1-500 (preferably 1:1-500:1-200, most preferably 1:10-250: 1.5-100). When the microchannel reaction unit is the above-mentioned microchannel reactor, the mass ratio of the auxiliary feed:the olefin raw material:the total amount of BF$_3$ gas refers to the mass ratio of the raw materials when all the raw materials are fed into the microchannel reactor, i.e., it can be the proportion of reaction raw materials in the stream immediately downstream of the fluid distributor.

In one embodiment of the present invention, according to the process of the present invention, the high-pressure separation unit is preferably a high-pressure separator. The pressure of the high-pressure separator can be 0.01-10 MPa, preferably 0.01-8 MPa, more preferably 0.1-6 MPa. The temperature of the high-pressure separator can be 0-120° C., preferably 10-80° C., more preferably 20-60° C. The volume of the high-pressure separator can be 0.1-20000 L, preferably 0.2-2000 L.

In one embodiment of the present invention, the low-pressure separation unit is preferably a low-pressure separator. The pressure of the low-pressure separator can be −0.1 to 1 MPa, preferably-0.1 to 0.9 MPa, more preferably-0.1 to 0.1 MPa. The temperature of the low-pressure separator can be 0-120° C., preferably 10-80° C., more preferably 20-60° C. The volume of the low-pressure separator can be 0.1-20000 L, preferably 0.2-2000 L.

In one embodiment of the present invention, the pressure of the recycled BF$_3$ gas through the gas circulation unit can be 0.01-10 MPa, preferably 0.01-8 MPa, more preferably 0.1-6 MPa.

In one embodiment of the present invention, the pressure of the pressure control unit is 0.01-10 MPa, preferably 0.01-8 MPa, more preferably 0.1-6 MPa.

In one embodiment of the present invention, according to the process of the present invention, the post-treatment method used in the post-treatment unit can be the post-treatment methods well known to those skilled in the art, and for example can be one or more of adsorption, extraction, distillation, centrifugation, sedimentation, alkaline washing and water washing. Preferably, the post-treatment method is sedimentation or centrifugation. The sedimentation or centrifugation enables the separation of the stream entering the post-treatment unit into a light liquid phase and a heavy liquid phase, the heavy liquid phase is the complex of auxiliary feed and $BF_3$ and the unreacted olefin raw material, and optionally returned to the mixing unit to continue the participation in the continuous reaction. The light liquid phase is a crude polyolefin product, which can be subjected to a further post-treatment.

In one embodiment of the present invention, according to the process of the present invention, preferably, a gas purification unit is provided between the low-pressure separation unit and the gas circulation unit, and/or, a gas purification unit is provided between the pressure control unit and the gas circulation unit. The gas purification unit enables drying and/or purifying the $BF_3$ gas entering therein. The gas purification unit can be one or more of a gas filter, an adsorption dryer, a freeze dryer and a cyclone separator, preferably an adsorption dryer, in which a filler can be filled up, and the filler can be one or more of silica gel, anhydrous calcium sulfate, anhydrous calcium chloride, and active carbon.

In one embodiment of the present invention, according to the process of the present invention, in the case that in the mixing unit, besides the olefin raw material and the auxiliary feed, the $BF_3$ gas is further mixed, based on the total mass of the whole $BF_3$ in the microchannel reaction unit, the mass ratio of the $BF_3$ gas that directly enters the microchannel reaction unit to the $BF_3$ gas that is mixed in the mixing unit is 100-10:0-90.

According to the process of the present invention, further preferably, fractionation, hydrogenation and optional blending operations are performed on the obtained polyolefin product to obtain a polyolefin product (synthetic oil) that meets the viscosity grade.

The process of the present invention has the advantages of high polymerization reaction speed, high reaction conversion and good product selectivity, and is suitable for large-scale industrial production.

In a third aspect, the present invention provides a process for preparing polyalpha-olefins using any of the apparatuses described in the first aspect.

The process for preparing polyalpha-olefins using any of the apparatuses described in the first aspect, according to the present invention, comprises: A mixed stream obtained after mixing an olefin raw material and an auxiliary feed in a mixing unit 1 and a $BF_3$ gas are each independently allowed to enter a microchannel reaction unit 2, an intermediate stream formed after the polymerization reaction in the microchannel reaction unit 2 is allowed to enter a high-pressure separation unit 3, the intermediate stream undergoes a first gas-liquid separation in the high-pressure separation unit 3, the separated liquid phase enters a low-pressure separation unit 4, a second gas-liquid separation occurs in the low-pressure separation unit 4, the liquid phase separated from the low-pressure separation unit 4 enters a post-treatment unit 6, and a polyolefin product is obtained after the treatment in the post-treatment unit; The gas phases separated from the high-pressure separation unit 3 and the low-pressure separation unit 4 ($BF_3$ gas) enter a gas circulation unit 5, and the $BF_3$ gas is recovered for the recycled use. Preferably, the $BF_3$ gas is further fed into the mixing unit 1, so that the $BF_3$ gas, the olefin raw material and the auxiliary feed are mixed in the mixing unit 1, and then the mixed stream and the $BF_3$ gas each independently enter the microchannel reaction unit 2. Optionally, the heavy liquid phase containing the complex of the auxiliary feed and $BF_3$ and the unreacted olefin raw material obtained after the treatment in the post-treatment unit 6 is recycled to the mixing unit 1.

In one embodiment of the present invention, the olefin in the olefin raw material is one or more of $C_3$-$C_{20}$ alpha-olefins, preferably one or more of $C_5$-$C_{15}$ alpha-olefins, more preferably one or more of $C_7$-$C_{14}$ alpha-olefins. For example, it can be the olefins commonly used in the preparation of PAO synthetic base oils, such as nonene and decene.

In one embodiment of the present invention, the olefin raw material can further contain $C_5$-$C_{20}$ alkane and/or $C_1$-$C_{20}$ oxygen-containing compound as solvent. Relative to the total mass of the olefin raw material, the mass fraction of the $C_5$-$C_{20}$ alkane can be 0-80%, preferably 0.5-50%, most preferably 1-30%. Relative to the total mass of the olefin raw material, the mass fraction of the $C_1$-$C_{20}$ oxygen-containing compound can be 0-20%, preferably 0-10%, most preferably 0.001-5%. The $C_5$-$C_{20}$ alkane can be one or more of n-alkane, iso-alkane and cycloalkane; the $C_1$-$C_{20}$ oxygen-containing compound can be one or more of n-alkanol, iso-alcohol and ketone. A Fischer-Tropsch olefin raw material can be used as the mixture of $C_3$-$C_{20}$ alpha-olefin, $C_5$-$C_{20}$ alkane, and $C_1$-$C_{20}$ oxygen-containing compound (namely the olefin raw material).

In one embodiment of the present invention, the auxiliary feed can be a commonly used auxiliary agent that can be used as an electron donor of $BF_3$, and can be one or more of an alcohol having a carbon atom number of 1-20, an ether having a carbon atom number of 1-20, an aldehyde having a carbon atom number of 1-20, a ketone having a carbon atom number of 1-20, an ester having a carbon atom number of 1-30, a carboxylic acid having a carbon atom number of 1-20 and a phenol having a carbon atom number of 1-20, preferably an alcohol having a carbon atom number of 1-10, more preferably an alcohol having a carbon atom number of 3-5, for example, one or more of n-propanol, iso-propanol, n-butanol, iso-butanol, n-pentanol and iso-pentanol.

According to the process of the present invention, the speed for the olefin raw material entering the mixing unit 1 is 10-5000 L/h, preferably 20-4000 L/h, more preferably 40-2500 L/h. The speed for the auxiliary feed entering the mixing unit 1 is 0.01-1000 L/h, preferably 0.1-800 L/h, more preferably 0.2-500 L/h. The gas-entering speed for the $BF_3$ gas entering the microchannel reaction unit 2 (including the initially injected $BF_3$ gas and the recycled $BF_3$ gas) is 5-200000 L/h, preferably 50-100000 L/h, more preferably 100-50000 L/h. Generally speaking, the gas-entering speed for the $BF_3$ gas entering the microchannel reaction unit 2 is controlled to be a constant value or within a numerical range, and the amount of the initially injected $BF_3$ gas can be adjusted according to the amount of the recycled $BF_3$ gas, as long as the total amount of the two is the constant value or within the numerical range. In the case of further feeding the $BF_3$ gas to the mixing unit 1, the speed for the $BF_3$ gas entering the mixing unit 1 is 4-180000 L/h, preferably 45-90000 L/h, more preferably 90-45000 L/h.

According to the process of the present invention, preferably, the reaction temperature in the microchannel reaction unit 2 is 0-120° C., preferably 10-80° C., more preferably 20-60° C. The reaction pressure in the microchannel reaction unit 2 is 0.01-10 MPa, preferably 0.01-8 MPa, more preferably 0.1-6 MPa. The residence time of the olefin raw material in the microchannel reaction unit 2 is 1-3600 seconds, preferably 10-1800 seconds, more preferably 15-1000 seconds. In the microchannel reaction unit 2, the mass ratio of the auxiliary feed:the olefin raw material:the total amount of $BF_3$ gas is 1:1-1000:1-500 (preferably 1:1-500:1-200, most preferably 1:10-250:1.5-100). When the microchannel reaction unit 2 is the above-mentioned microchannel reactor, the mass ratio of the auxiliary feed:the olefin raw material:the total amount of $BF_3$ gas refers to the mass ratio of the raw materials when all the raw materials are fed into the microchannel reactor, i.e., it can be the proportion of reaction raw materials in the stream immediately downstream of the fluid distributor.

According to the process of the present invention, preferably, the high-pressure separation unit 3 is preferably a high-pressure separator. The pressure of the high-pressure separator can be 0.01-10 MPa, preferably 0.01-8 MPa, more preferably 0.1-6 MPa. The temperature of the high-pressure separator can be 0-120° C., preferably 10-80° C., more preferably 20-60° C. The volume of the high-pressure separator can be 0.1-20000 L, preferably 0.2-2000 L.

The low-pressure separation unit 4 is preferably a low-pressure separator. The low-pressure separation unit 4 is preferably a low-pressure separator. The pressure of the low-pressure separator can be –0.1 to 1 MPa, preferably-0.1 to 0.9 MPa, more preferably-0.1 to 0.1 MPa. The temperature of the low-pressure separator can be 0-120° C., preferably 10-80° C., more preferably 20-60° C. The volume of the low-pressure separator can be 0.1-20000 L, preferably 0.2-2000 L.

The pressure of the recycled $BF_3$ gas through the gas circulation unit 5 can be 0.01-10 MPa, preferably 0.01-8 MPa, more preferably 0.1-6 MPa.

The pressure of the pressure control unit 7 can be 0.01-10 MPa, preferably 0.01-8 MPa, more preferably 0.1-6 MPa.

The process of the present invention has the advantages of high polymerization reaction speed, high reaction conversion and good product selectivity, and is suitable for large-scale industrial production.

DESCRIPTION OF THE REFERENCE NUMERALS

Figure 1:
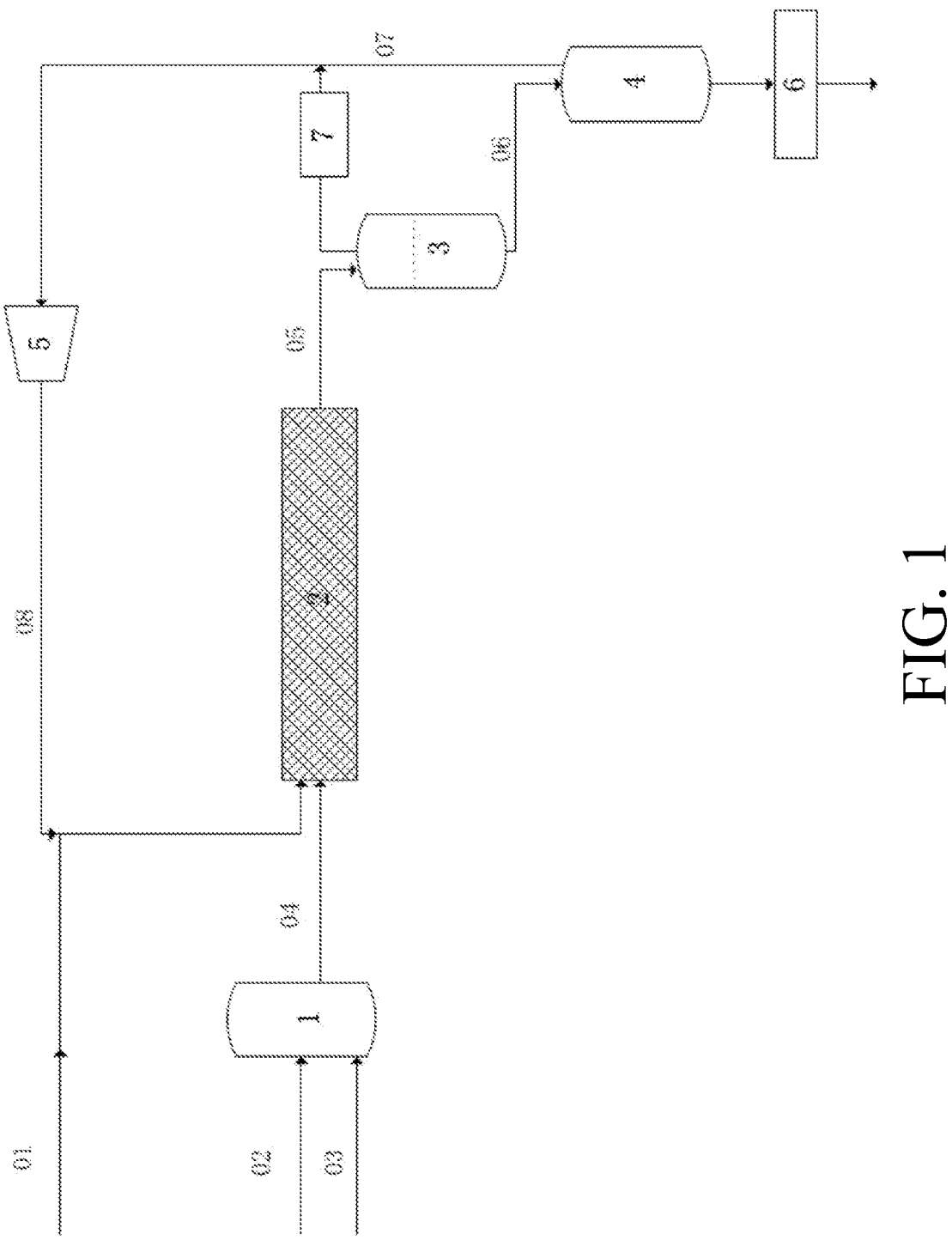
FIG. 1 is a schematic diagram of the apparatus of the present invention.

1: Mixing unit (preferably mixer)
2: Microchannel reaction unit (preferably microchannel reactor)
3: High-pressure separation unit (preferably high-pressure separator)
4: Low-pressure separation unit (preferably low-pressure separator)
5: Gas circulation unit
6: Post-treatment unit
7: Pressure control unit
8: Gas purification unit
01: $BF_3$ gas inlet
02: Auxiliary feed inlet
03: Olefin raw material inlet
04 to 09: Pipelines
001: Discharge pipe
002: Feed pipe
003: Shell
004: First heat exchange medium inlet
005: First heat exchange medium outlet
006: Second heat exchange medium inlet
007: Second heat exchange medium outlet
008: Mixing zone
009: Reaction zone
010: Reaction channel
011: Second mixing member
012: Second heat exchange cavity
013: First heat exchange cavity
014: Mixing channel
015: First mixing member
016: Fluid distributor
017: Fluid distribution pipe
018: Discharge pipe
019: First partition plate
020: Transition zone
021: Stabilization channel
022: Diffusion channel
023: Feeding zone
024: Collection zone
025: Second partition plate
0001: Main flow passage
0002: Branch flow passage
0003: Collection cavity
0004: Base strip
0005: Tooth element

DETAILED DESCRIPTION

The present invention will be further described below through examples and in conjunction with the accompanying drawings.

It should be noted that, in some examples of the present invention, the apparatus for preparing polyalpha-olefins can realize the continuous production as long as the temperature and pressure of the microchannel reaction unit can be controlled, so the process parameters or process conditions for all operation units in the apparatus of the present invention are not listed nor indispensably listed.

FIG. 1 is a schematic diagram of the apparatus for preparing polyalpha-olefins of the present invention, the apparatus comprises a mixing unit 1, a microchannel reaction unit 2, a high-pressure separation unit 3, a low-pressure separation unit 4, a gas circulation unit 5, a post-treatment unit 6 and a pressure control unit 7, the mixing unit 1, the microchannel reaction unit 2, the high-pressure separation unit 3, the low-pressure separation unit 4, and the gas circulation unit 5 are successively connected, the microchannel reaction unit 2 is provided with the $BF_3$ gas inlet 01, the mixing unit 1 is provided with the auxiliary feed inlet 02, and the olefin raw material inlet 03, the gas circulation unit 5 is connected with the $BF_3$ gas inlet 01, the low-pressure separation unit 4 is further connected with the post-treatment unit 6, the high-pressure separation unit 3, the pressure control unit 7, and the gas circulation unit 5 are further successively connected.

Figure 2:
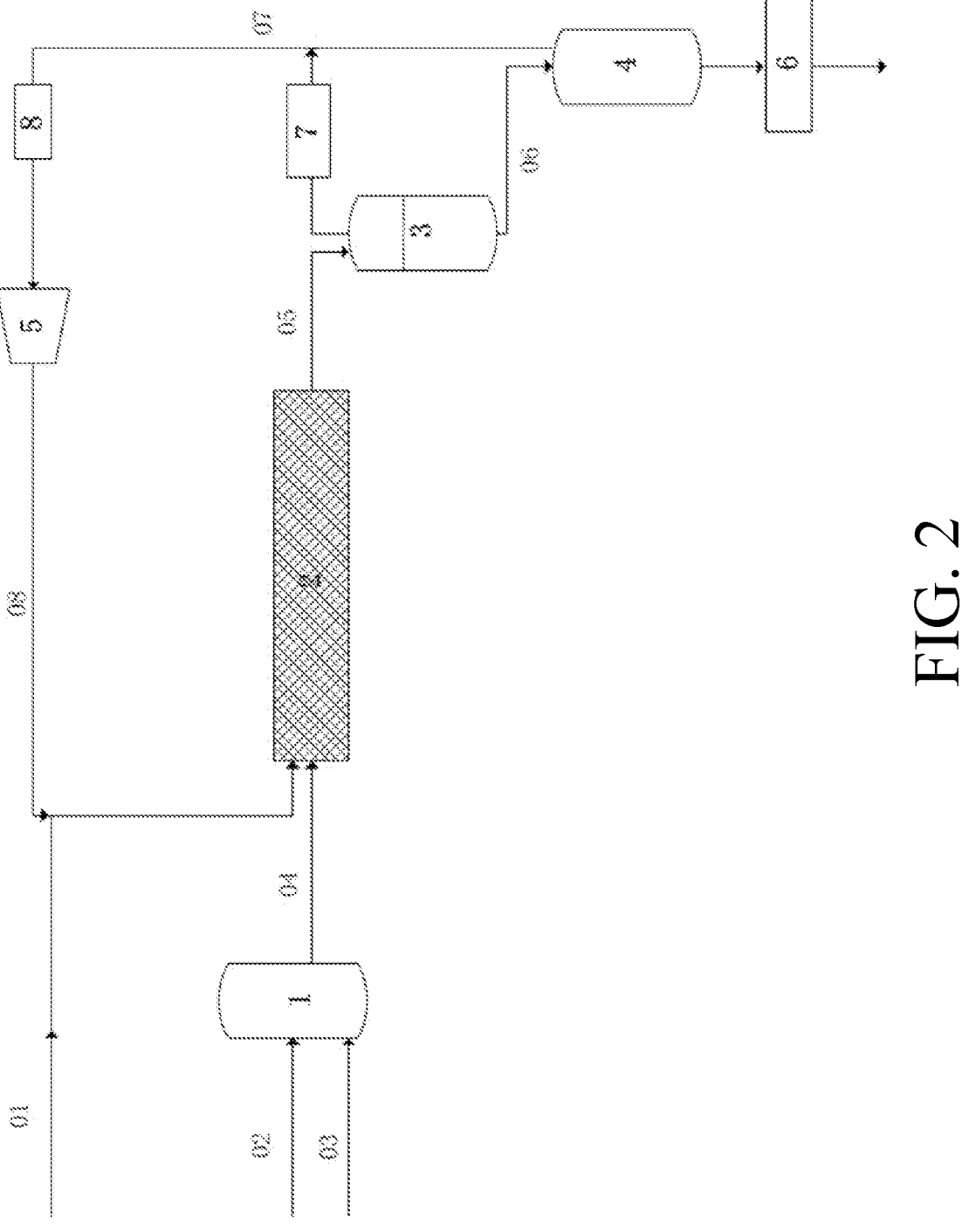
FIG. 2 is a schematic diagram of the preferred apparatus of the present invention.

FIG. 2 is a schematic diagram of the apparatus for preparing polyalpha-olefins of the present invention, which is formed based on the apparatus in FIG. 1 by arranging one gas purification unit 8 in common between the pressure control unit 7 and the gas circulation unit 5, and between the low-pressure separation unit 4 and the gas circulation unit 5.

Figure 3:
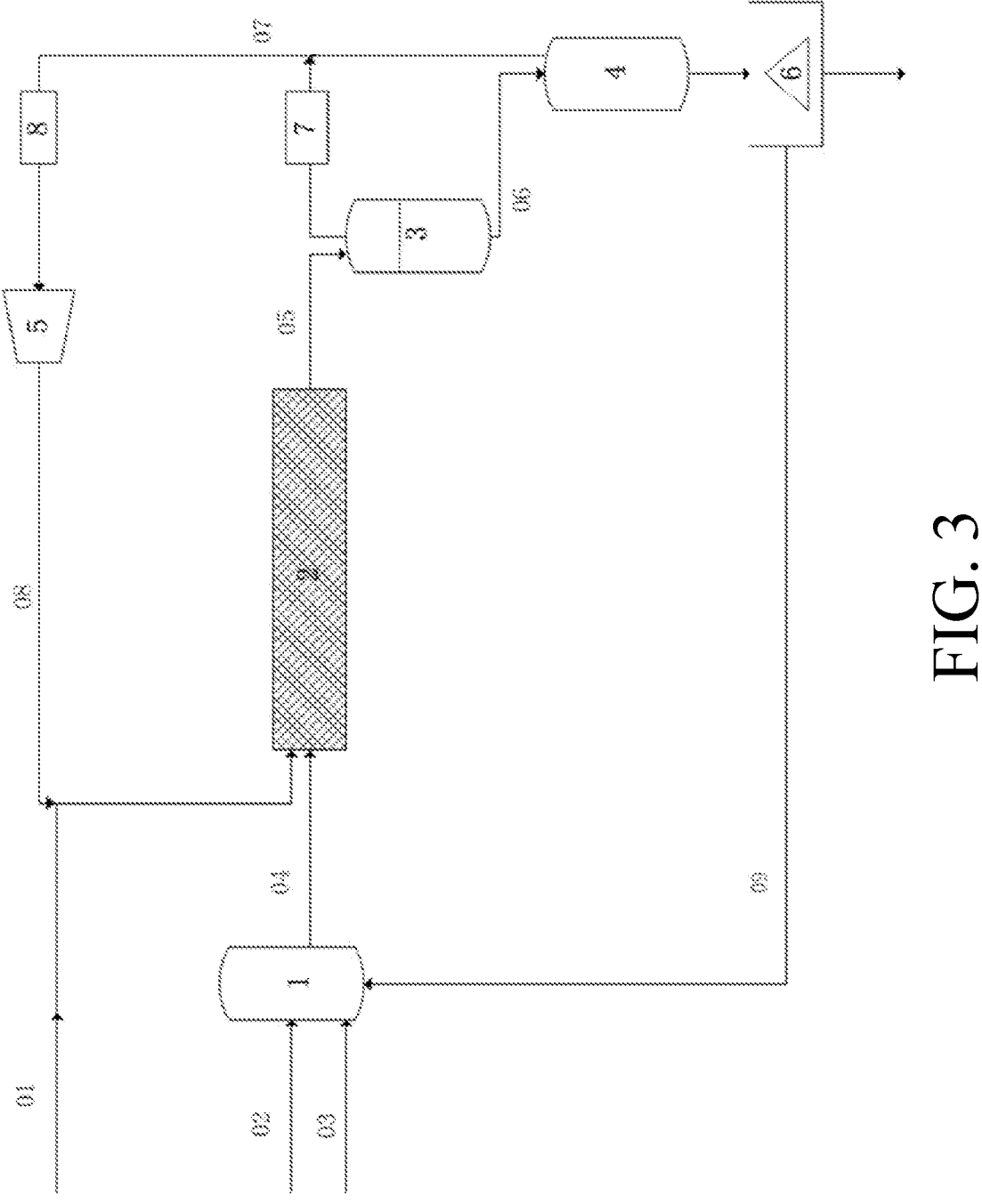
FIG. 3 is a schematic diagram of the preferred apparatus of the present invention.

FIG. 3 is a schematic diagram of the apparatus for preparing polyalpha-olefins according to the present invention, which is different from the apparatus of FIG. 2 in that the post-treatment unit 6 is connected with the mixing unit 1. In said figure, the post-treatment unit 6 is a sedimentation device or a centrifugation device, the sedimentation device or centrifugation device enables the separation of the stream entering therein into a light liquid phase and a heavy liquid phase, and the heavy liquid phase (containing the complex of auxiliary feed and $BF_3$ and the unreacted olefin raw material) is returned to the mixing unit 1 to continue the continuous reaction.

Figure 4:
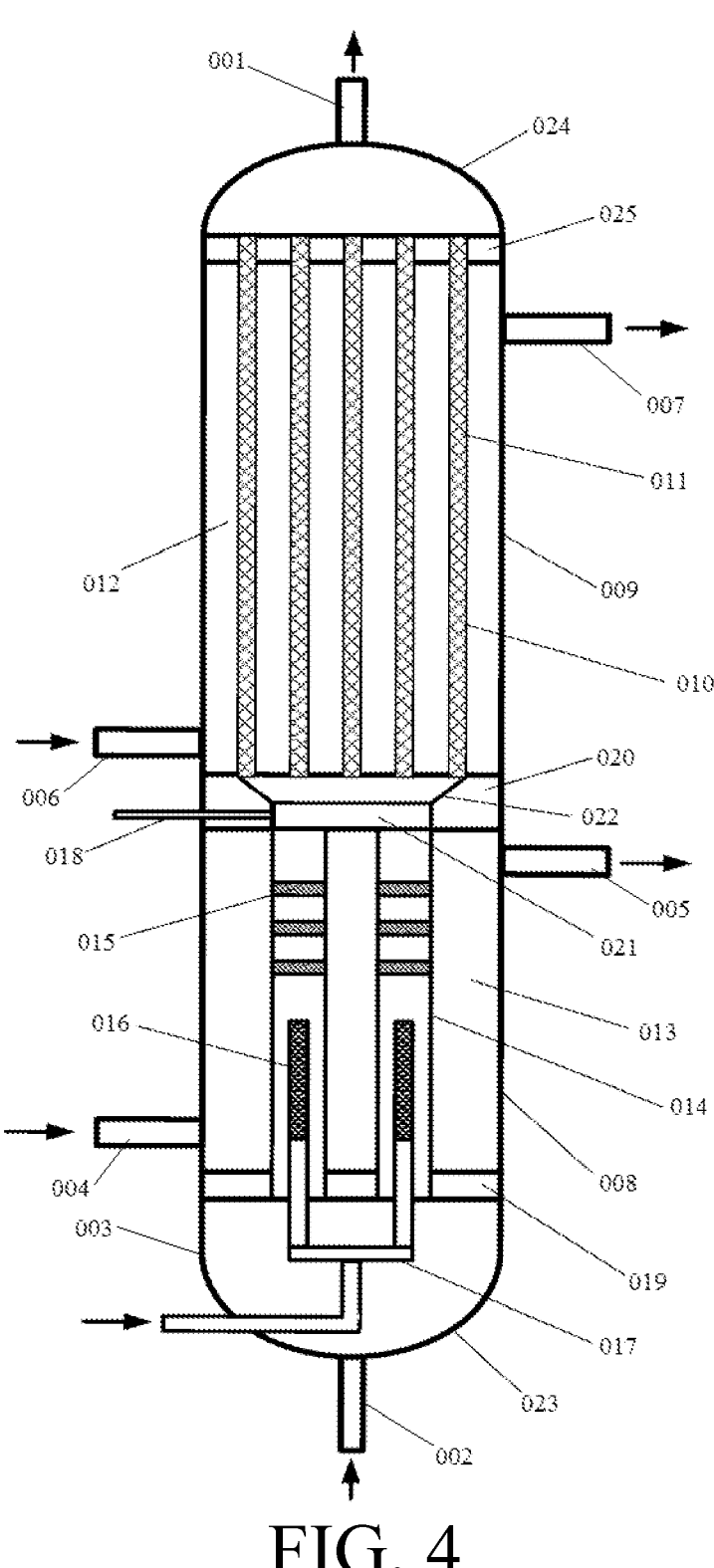
FIG. 4 is a schematic diagram of the preferred microchannel reactor of the present invention.

The microchannel reaction unit 2 of the present invention is preferably the microchannel reactor shown in FIG. 4.

The preferred microchannel reactor of the present invention comprises:

a shell 003; a feeding zone 023, a mixing zone 008, a reaction zone 009, and a collection zone 024 are successively arranged and communicated along a first direction in the shell 003, wherein the shell 003 is provided with a feed pipe 002 communicated with the feeding zone 023 and a discharge pipe 001 communicated with the collection zone 024, and the mixing zone 008 is provided with a mixing channel 014 extending along the first direction;

a fluid distribution pipe 017, the fluid distribution pipe 017 is extended from the exterior of the shell 003 into the mixing channel 014, the fluid distribution pipe 017 is connected with a fluid distributor 016 at an end of the mixing channel 014.

The shell 003 is the main container for accommodating the reactant and the product, and the feeding zone 023, the mixing zone 008, the reaction zone 009 and the collection zone 024 are different zones of the inner space of the shell 003 (all of which can store the stream), these zones are arranged in a straight line so that the reactant (and the product) advances in a straight line. In the present invention, the flow direction of the stream is referred to as the first direction. Preferably, as shown in FIG. 4, the shell 003 is positioned such that the first direction is the elevation direction, and the feeding zone 023, the mixing zone 008, the reaction zone 009 and the collection zone 024 are arranged in a bottom-to-top direction.

A first group of the reaction stream (the stream from the mixing unit 1) can be supplied into the feeding zone 023 through the feed pipe 002 on the shell 003, and the feeding zone 023 has a relatively large cavity and can act as storing the first group of the reaction stream, the first group of the reaction stream in the feeding zone 023 can enter the adjacent mixing zone 008, that is, the mixing channel 014. The fluid distribution pipe 017 is connected to the $BF_3$ gas inlet 01, hence the input of a second group of the reaction stream (the individually fed $BF_3$ gas) can be provided to the mixing channel 014 through the fluid distribution pipe 017, so as to allow mixing the first group of the reaction stream and the second group of the reaction stream each other in the mixing channel 014 of the mixing zone 008. Among others, the outlet end of the fluid distribution pipe 017 is provided with a fluid distributor 016. The fluid distributor 016 can form the second group of the reaction stream into smaller droplets or bubbles, so that the second group of the reaction stream can be more uniformly distributed to the first group of the reaction stream in the mixing channel 014. Among others, the mixing structure in the mixing channel 014 is more suitable for mixing the liquid-phase stream and the gas-phase stream. At this time, the first group of the reaction stream is a liquid-phase stream, and the second group of the reaction stream is a gas-phase stream. The gas-phase stream can be formed into dispersed micro-bubbles through the fluid distributor 016 to increase the contact area with the liquid-phase stream, and at the same time, also can impact the liquid-phase stream to a greater extent, thereby improving the uniformity of mixing the two.

In addition, as shown in FIG. 4, the mixing channel 014 is a cavity extending along the first direction, that is, the mixing channel 014 has a substantially tubular structure, thereby allowing the stream therein to flow along the first direction to form a stable plug flow.

The preferred microchannel reactor provided by the present invention, by designing the structure of the mixing channel and the mixing mode therein, can realize continuous and efficient mixing of the reaction stream and at the same time can maintain the reaction fluid to flow in a plug flow-like manner, ensure the consistency of the residence time of the reaction fluid as much as possible, and avoid the undesirable product selectivity due to residence time distribution.

More specifically, the fluid distributor 016 is at least one selected from powder sintered body with micropores, mesoporous foam material, wire mesh, tube with microslits or micropores. The powder sintered body with micropores can be obtained by sintering the powder into a structure with micropores through a powder metallurgy process, the hollow/mesoporous foam material is a hollow microchannel with network skeletons, and the wire mesh is a network structure with micropores, and the tube is provided with microslits or microholes, all of which can disperse the fluid from the fluid distributor tube 017 into smaller bubbles or droplets.

Preferably, the fluid distributor 016 is a cylindrical powder sintered body with micropores, and the mixing channel 014 has a circular cross-section. The fluid distributor 016 may be a structure having the substantially same outer diameter as the fluid distribution pipe 017, the cross-sectional shape of the fluid distributor 016 substantially corresponds to the cross-sectional shape of the mixing channel 014, and the fluid distributor 016 can be arranged coaxially with the mixing channel 014 so as to allow the fluid stream dispersed by the fluid distributor 016 to be more uniformly mixed with the stream in the mixing channel 014, and form a stable and uniform plug flow to avoid the inconsistency in the residence time of the stream.

Among others, the fluid distributor 016 has a cross-sectional area of 0.01 cm2-200 cm2, and a length of 1 mm-2000 mm. The mixing channel 014 has a cross-sectional area of 0.05 cm2-400 cm2, and a length of 50 mm-5000 mm. The length and the cross-sectional area of the mixing channel 014 are both greater than the length and the cross-sectional area of the fluid distributor 016.

In addition, the mixing zone 008 is provided with 1-100 (preferably 1-50, more preferably 2-10) mixing channels 014, the fluid distribution pipe 017 includes a main pipe extending from the exterior of the shell 003 into the feeding zone 023 and branch pipes extending from the feeding zone 023 into each mixing channel 014 with fluid distributors 016 connected to branch pipe ends. A plurality of mixing channels 014 are respectively communicated with the feeding zone 023, and the first group of the reaction stream is divided into a plurality of parts in the mixing channels, which play the role of dispersing the first group of the reaction stream, and allow the first group of the reaction stream to form the stable, uniform plug flow. The fluid distribution pipe 017 includes a main pipe and branch pipes, wherein the main pipe is connected to the $BF_3$ gas inlet 01, and extends from the position of the shell 003 corresponding to the feeding zone 023 into the feeding zone 023, and the branch pipes extend from the feeding zone 023 into the mixing channels 014. That is, the fluid distribution pipe 017 extends from the feeding zone 023 into the mixing channels 014. The mixing zone 008 and the feeding zone 023 can be partitioned by a first partition plate 019. The first partition plate 019 is provided with a plurality of through holes, and each mixing channel 014 is aligned with each through hole, so that the mixing zone 008 is communicated with the feeding zone 023.

In addition, in the mixing channel 014, a first mixing member 015 is disposed downstream of the fluid distributor 016. In the mixing channel 014, the downstream of the fluid distributor 016 refers to the downstream of the fluid flow direction (i.e., the downstream of the fluid distributor 016 in the first direction), that is, the position closer to the reaction zone 009 than the fluid distributor 016. Through the first mixing member 015, the fluid can be further mixed to improve the mixing uniformity of the two groups of streams.

Figure 5:
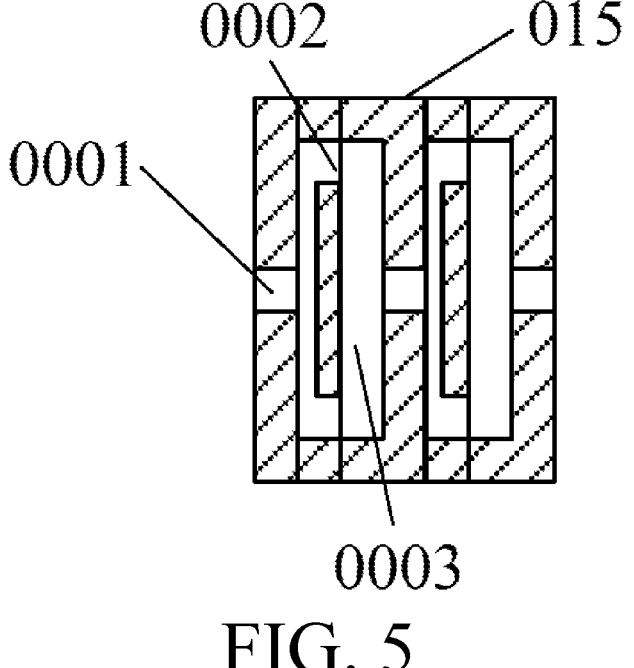
FIG. 5 is a sectional view of the first mixing member according to the embodiment of the present invention.

Specifically, the first mixing member 015 is provided with a main flow portion and a branch flow portion that are alternately arranged and communicated along the first direction. The main flow portion is provided with a single main flow passage 0001, and the branch flow portion is provided with a plurality of branch flow passages 0002. As shown in FIG. 5, one or more main flow portions/branch flow portions may be provided respectively and arranged alternately, wherein only a single main flow passage 0001 is arranged in the main flow portion, and a plurality of branch flow passages 0002 are arranged in the branch flow portion. The fluid converges in the main flow passage 0001 and disperses in the branch flow passages 0002 of each branch flow portion. Through such a converging-dispersing process, the degree of turbulence can be fully increased and the mixing uniformity of the fluid can be improved.

Further, in the first mixing member 015, the collection cavity 0003 that is communicated with a plurality of branch flow passages 0002 is disposed downstream of the branch flow portion 0002. As shown in FIG. 5, the volume (especially the cross-sectional area) of the collection cavity 0003 is larger than the volume (especially the cross-sectional area) of the main flow passage 0001, and the collection cavity 0003 can converge a plurality of upstream branch flow passages 0002 together, and it is communicated with the next main flow passage 0001 or the next stage of the reaction zone 009 or the transition zone 020.

As shown in FIG. 5, the first mixing member 015 according to an embodiment of the present invention is shown, which is formed by splicing a plurality of plate members (the number can be 2-100, preferably 2-50, more preferably 10-30) (the thickness is about 0.2 mm-10 mm) arranged along the first direction, and the structures such as holes and cavities that correspond to the main flow passage 0001, the branch flow passage 0002 and the collection cavity 0003 are formed on each plate member, which is convenient for processing and manufacturing.

In addition, the mixing zone 008 comprises a first heat exchange cavity disposed in the shell 003, the mixing channel 014 is disposed in the first heat exchange cavity 013, the shell 003 is provided with a first heat exchange medium inlet 004 and a first heat exchange medium outlet 005 that are communicated with the first heat exchange cavity 013. In the mixing zone 008, the mixing channel 014 and the first heat exchange cavity 013 are isolated from each other and not communicated with each other, but the heat conduction can be achieved between each other, and pipe fittings with good thermal conductivity can be used in the mixing channel 014. By supplying the heat exchange medium to the first heat exchange medium inlet 004 and discharging the heat exchange medium through the first heat exchange medium outlet 005, a circulating flow of the heat exchange medium can be formed in the first heat exchange cavity 013 to realize the heat exchange with the mixing channel 014 and the fluid therein, that is, to realize the heat dissipation of the mixing channel 014 and the fluid therein, ensure that the heat generated by the mixing and dissolving of the fluid in the mixing channel 014 is dissipated in time, so that the fluid therein is in a suitable temperature range.

Among others, the volumetric ratio of the first heat exchange cavity 013 to the mixing channel 014 is 2-50, preferably, the volumetric ratio of the first heat exchange cavity 013 to the mixing channel 014 is 5-30. The volume of the first heat exchange cavity 013 is larger than the volume of the mixing channel 014 so that the heat generated by the mixing and dissolving of the first group of the reaction stream and the second group of the reaction stream is conducted out in time.

In addition, a transition zone 020 is provided between the mixing zone 008 and the reaction zone 009, the transition zone 020 is provided with a stabilization channel 021 with constant cross-section and a diffusion channel 022 with gradually enlarged cross-section arranged and communicated along the first direction, the stabilization channel 021 is communicated with the mixing channel 014, the diffusion channel 022 is communicated with the reaction zone 009. The transition zone 020 can converge the mixed fluids from a plurality of the mixing channels 014 together in the stabilization channel 021 to achieve another uniform mixing, and then deliver the mixed fluids into the reaction zone 009 via the diffusion channel 022. Among others, the transition area 020 is provided with a stabilization channel 021 and a diffusion channel 022, the stabilization channel 021 mainly realizes the converging and mixing of the fluids, and the diffusion channel 022 is in a bell mouth shape, which can diffuse, for example, can disperse the mixed fluid into a plurality of the reaction channel 010 as described hereinafter. The two ends of the transition zone 020 are respectively provided with partition plates with through holes, so as to be respectively isolated from the mixing zone 008 (mainly the first heat exchange cavity 013) and the reaction zone 009 (mainly the second heat exchange cavity 012), and communicated with each mixing channel 014 and each reaction channel 010 through each through hole on each partition plate, and the diffusion channel 022 and the stabilization channel 021 can be pipe fittings provided between two partition plates.

In addition, the stabilization channel 021 can be connected to a discharge pipe 018 extending to the exterior of the shell 003. As mentioned above, the stabilization channel 021 has the function of converging and mixing, and the discharge pipe 018 can discharge the bubbles and streams accumulated in the stabilization channel 021 to avoid the influence of the bubble accumulation on the mixing uniformity, and the blockage of streams. A valve can be set on the discharge pipe 018, and the valve can be opened when it is necessary to discharge bubbles or streams.

In addition, the diffusion channel 022 is provided with a diffusion plate with meshes or slits. The diffusion plate may be substantially perpendicular to the first direction. The fluid in the diffusion channel 022 can flow through meshes or slits on the diffusion plate, so that the fluid is dispersed and the uniformity of the mixed fluid is enhanced.

The reaction zone 009 is provided with a plurality of parallel reaction channels 010 extending along the first direction and communicated with the mixing channel 014 via the stabilization channel 021 and the diffusion channel 022. The reaction channel 010 provides a reaction space for the mixed fluid, and bears the mixed fluid to flow to the next stage of the collection area 024 along the first direction, so that the mixed fluid reacts while forming a stable plug flow in the reaction channel 010 to avoid undesired products due to inconsistent residence time distributions. As stated above, a transition zone 020 may be provided between the reaction zone 009 and the mixing zone 008, and a plurality of reaction channels 010 may be communicated with the diffusion channel 022, so that the mixed fluid in the diffusion channel 022 is uniformly dispersed into a plurality of the reaction channels 010. The number of reaction channels is, for example, 2-10000 channels, preferably 2-5000 channels, and more preferably 2-500 channels. The reaction channel 010 can have a cross-section in at least one of circular, rectangular and triangular shapes.

In addition, the reaction channel 010 is provided with a second mixing member 011, and the second mixing member 011 includes a base strip 0004 extending along the first direction and a tooth element 0005 connected to the base strip 0004 and extended transversely to the base strip 0004. In the second mixing member 011, the base strip 0004 provides a support for a plurality of tooth elements 0005, so that the tooth elements 0005 can be stably held in the reaction channel 010, and the tooth elements 0005 extend approximately transversely to the reaction channel 010, which can improve the turbulence degree of the fluid in the reaction channel 010, thereby improving the mixing uniformity between the reaction streams.

Among others, the tooth elements 0005 are in one of triangular, arcual, wavy, and spiral shapes. Tooth elements 0005 can be in various shapes, as long as they extend transversely to the reaction channel 010 and can achieve the effect of increasing the turbulence degree of the fluid.

Preferably, the tooth element 0005 is of triangular shape, and on one side of the triangle adjacent to the base strip 0004, one corner is connected to the base strip 0004, and the other corner is 0.01 mm-20 mm away from the base strip 0004. The tooth elements 0005 may be triangular plate members and are connected to the base strip 0004 only with one corner.

Preferably, each reaction channel 010 is provided with a plurality of the second mixing members 011 (the number can be 2-100, preferably 2-50, more preferably 10-30), which are stacked at intervals, and a plurality of the second mixing members 011 are stacked at intervals, and correspondingly the tooth elements 0005 are also stacked at intervals, and the tooth elements 0005 of different second mixing members 011 are arranged staggeredly, so that different second mixing members 011 are arranged more irregularly and the turbulence degree of the fluid in the reaction channel 010 can be better improved.

Preferably, the cross-section of the reaction channel 010 is rectangular, and the tooth elements 0005 extend between a set of opposite sides of the rectangle. Specifically, the reaction channel 010 includes four side walls, namely two sets of opposite parallel side walls, the base strip 0004 is disposed at one side wall of the reaction channel 010, and the tooth elements 0005 extend toward the other opposite side wall, a plurality of second mixing elements 011 can better accommodate the inner cavity structure having a square pillar shape of the reaction channel 010.

The reaction channel 010 has a cross-sectional area of 1 mm²-150 mm², and a length of 50 mm-5000 mm, the minimum distance between the reaction channels 010 is 1 mm-50 mm, and the second mixing member 011 has a thickness of 0.1 mm-3 mm, and the spacing between adjacent tooth elements 0005 is 1 mm-50 mm.

Preferably, the reaction channel 010 has a length of 100 mm-3000 mm, the minimum spacing between the reaction channels 010 is 3 mm-30 mm, the second mixing member 011 has a thickness of 0.2 mm-2 mm, the spacing between adjacent tooth elements 0005 is 1.5 mm-20 mm. The minimum spacing of the reaction channels 010 reflects the density of the reaction channels 010 in the reaction zone 009. Preferably, in the second mixing member 011, the tooth element 0005 is a plate member that can be coplanar with the base strip 0004, and the thickness of the second mixing member 011 is approximately the thickness of the tooth element 0005.

In addition, the reaction zone 009 can be provided with a second heat exchange cavity 012 disposed in the shell 003, the reaction channel 010 is disposed in the second heat exchange cavity 012, the shell 003 is provided with a second heat transfer medium inlet 006 and a second heat transfer medium outlet 007 that are communicated with the second heat exchange cavity 012. The second heat exchange cavity 012 may be mainly formed by the shell 003, and at two ends are respectively the second partition plate 025 between the reaction zone 009 and the collection zone 024 and the partition plate between the reaction zone 009 and the transition zone 020. Through the second heat exchange medium inlet 006 and the second heat exchange medium outlet 007, the heat exchange medium can be introduced into the second heat exchange cavity 012 to realize the heat exchange treatment of the reaction channel 010, so as to ensure that the fluid in the reaction channel 010 is reacted in an appropriate temperature range, and avoid the production of undesired products.

In addition, the first heat exchange cavity 013 and the second heat exchange cavity 012 may be connected in series with each other and arranged in a single heat exchange circulation flow path, or may also be arranged in parallel in a single heat exchange circulation flow path, or may be arranged in two different heat exchange circulation flow paths respectively.

Among others, the volumetric ratio of the second heat exchange cavity 012 to the reaction channel 010 is 2-50, preferably, the volumetric ratio of the second heat exchange cavity 012 to the reaction channel 010 is 5-30. The volume of the second heat exchange cavity 012 is larger than the volume of the reaction channel 010, so that the heat in the reaction channel 010 can be discharged in time to ensure that the reaction channel 010 is at a suitable temperature.

In the embodiments of the present invention, the preferred structural components or parameters are employed without repeated recitation when using the preferred microchannel reactor, unless otherwise specified.

The preferred microchannel reactor of the present invention can be used to synthesize polyalpha-olefin synthetic oil, the feed pipe 002 can be used to input the mixture of olefin raw material and auxiliary feed, and the fluid distribution pipe 017 can be used to input $BF_3$ gas. The mixture of olefin raw material and auxiliary feed is used as the continuous phase to enter the feeding zone 023 of the microchannel reactor from the feed pipe 002, and the $BF_3$ gas (having a weight ratio of $BF_3$ gas to alpha-olefin of 0.1% to 4%) is used as the dispersed phase to enter the mixing channel 014 of the reactor from the fluid distribution pipe 017. $BF_3$ is supplied in the gaseous form, and partially dissolved in the continuous phase through the fluid distributor 016. The mixed fluid that has completed the reaction in the reaction channel 010 enters the collection area 024, and finally is discharged from the discharge pipe 001. Preferably, a mixture of olefin raw material, auxiliary feed and $BF_3$ gas is fed from the feed pipe 002.

Figure 8:
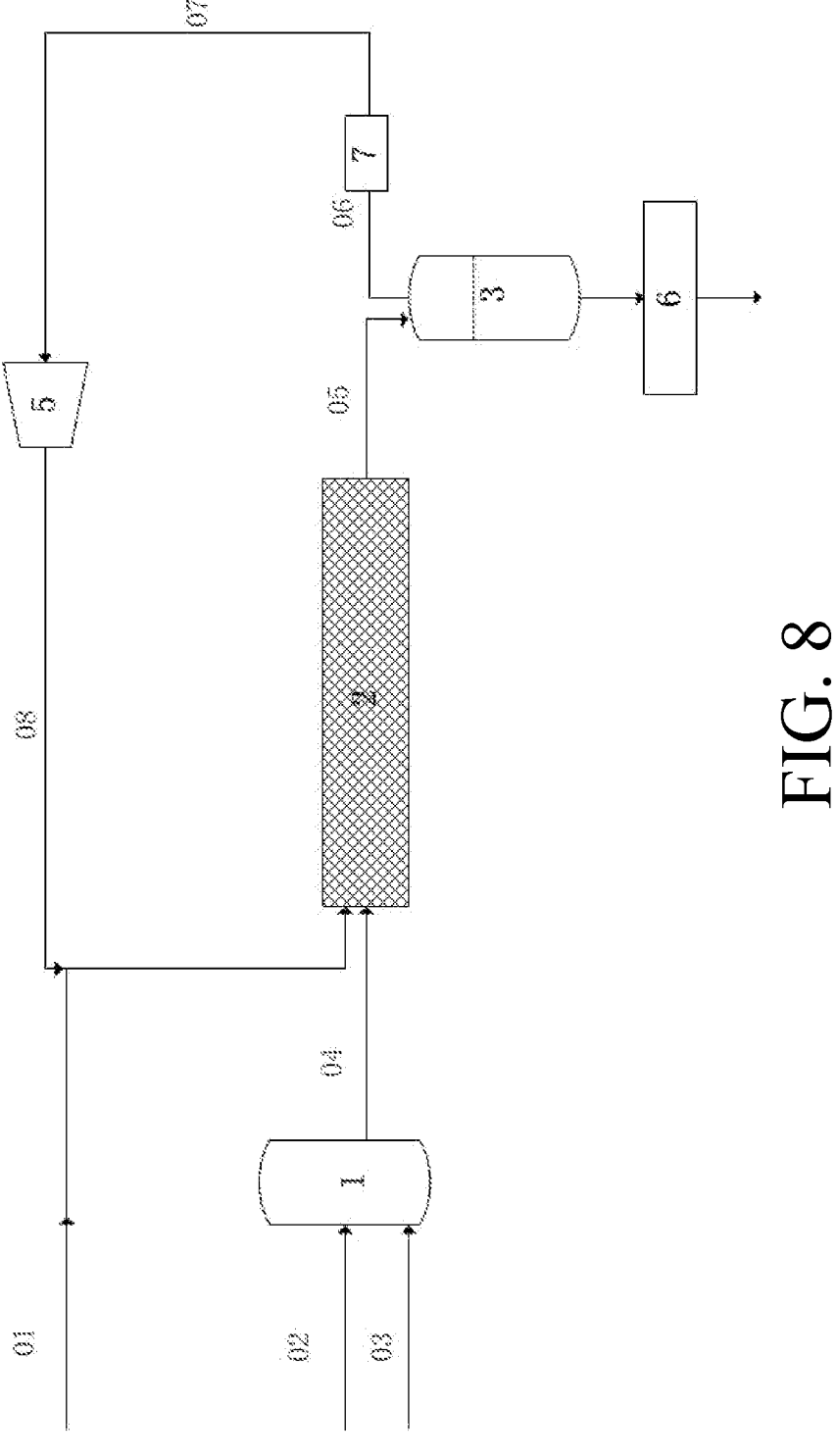
FIG. 8 is a schematic diagram of the comparative apparatus of the present invention.

FIG. 8 is a schematic diagram of the comparative apparatus of the present invention, which is different from the apparatus in in that there is only one high-pressure separation unit 3 and no low-pressure separation unit 4, and the high-pressure separation unit 3 is directly connected to the pressure control unit 7.

Example 1

The polymerization of the olefin raw material was carried out by using the apparatus shown in FIG. 1. In the apparatus, the mixing unit 1 was a mixer, the microchannel reaction unit 2 was a common microchannel reactor filled with mixing sheets (not the preferred microchannel reactor of the present invention), the high-pressure separation unit 3 was a high-pressure separator, the low-pressure separation unit 4 was a low-pressure separator, the gas circulation unit 5 was a compressor, the post-treatment unit 6 was a water washing device, and the pressure control unit 7 was a back pressure valve.

In the apparatus, the structure and parameter of the mixer was as follows: the allowable process fluid temperature range: 20-200° C., the upper limit of the working pressure (25° C.): 10 MPa; the structure and parameter of the microchannel reactor was as follows: 8 channels in parallel, the process fluid temperature range: −20 to 200° C., the maximum allowable reaction pressure: 6 MPa, the maximum allowable heat transfer medium pressure: 2 MPa, including two temperature probes for measuring the temperature in the reaction system, the fluid channel volume (without mixing disk): 50 mL, the reaction volume (in case of filling the mixing sheets) 30 mL, the volume flow rate: 3-30 L/h, with a header pipe for introducing the reaction gas and branch pipes for distributing the reaction gas to each channel; the high-pressure separator had a volume of 1 L, and a diameter of 10 cm; the low-pressure separator had a volume of 15 L and a diameter of 50 cm; the working parameter of the compressor was as follows: suction pressure: −0.1 to 0.03 MPa, exhaust pressure: 10 MPa, volumetric flow rate 3 m³/h; the back pressure valve had a pressure of 6 MPa; the dryer had an effective volume of 10 L, with a gas distributor at the bottom, silica gel filler disposed in the upper layer.

The mixed stream obtained by mixing 1-nonene and n-butanol in the mixer, and the $BF_3$ gas were each independently passed into the microchannel reactor, $BF_3$ entered the microchannel reactor through the reaction gas header pipe, and the volume flow rate of $BF_3$ was 52 L/h, the volume flow rate of 1-nonene was 10 L/h, and the volume flow rate of n-butanol was 0.1 L/h. The polymerization reaction was performed in the microchannel reactor, the reaction temperature was 20° C., and the pressure was 4 MPa. The formed intermediate stream entered the high-pressure separator. The intermediate stream underwent the first gas-liquid separation in the high-pressure separator. The separation temperature was 20° C. and the separation pressure was 4 MPa. The separated liquid phase entered the low-pressure separator for the second gas-liquid separation, the separation temperature was 20° C., and the separation pressure was-0.01 MPa. The liquid phase separated from the low-pressure separator was water-washed with the water washing device to obtain the polyolefin product. The $BF_3$ gases separated from the high-pressure separator and the low-pressure separator were recycled by the compressor. The gas outlet pressure of the compressor was 4 MPa. After the system run stably, a small amount of polyolefin product sample in the low-pressure separator was taken, water washed, and measured by the gas chromatography for the content of each component in the product. The $BF_3$ gas recovery was 40%. The test results were as shown in Table 1.

TABLE 1

| Sample olefin composition distribution | Content |
|---|---|
| Monomer, % | 3.3 |
| Dimer, % | 8.1 |
| Trimer, % | 38.9 |
| Tetramer, % | 28.3 |
| Pentamer, % | 17.2 |
| ≥Hexamer, % | 4.2 |
| Conversion, % | 96.7 |

Comparative Example 1

The low-pressure separator was removed from the apparatus used in Example 1, wherein the high-pressure separator was directly successively connected to the back pressure valve and the compressor, and the high-pressure separator was directly connected to the water washing device of the post-treatment unit.

The polymerization of the olefin raw material was carried out by using the above-mentioned apparatus. In the apparatus, the structure and parameter of the mixer was as follows: the allowable process fluid temperature range: 20-200° C., the upper limit of the working pressure (25° C.): 10 MPa; the structure and parameter of the microchannel reactor was as follows: 8 channels in parallel, the process fluid temperature range: −20 to 200° C., the maximum allowable reaction pressure: 6 MPa, the maximum allowable heat transfer medium pressure: 2 MPa, including two temperature probes for measuring the temperature in the reaction system, the fluid channel volume (without mixing disk): 50 mL, the reaction volume (in case of filling the mixing sheets) 30 mL, the volume flow rate: 3-30 L/h, with a header pipe for introducing the reaction gas and branch pipes for distributing the reaction gas to each channel; the high-pressure separator had a volume of 1 L, and a diameter of 10 cm; the working parameter of the compressor was as follows, suction pressure: −0.1 to 0.03 MPa, exhaust pressure: 10 MPa, volumetric flow rate 3 m³/h; the back pressure valve had a pressure of 6 MPa; the dryer had an effective volume of 10 L, with a gas distributor at the bottom, silica gel filler disposed in the upper layer.

The mixed stream obtained by mixing 1-decene and isopropanol in the mixer, and the $BF_3$ gas were each independently passed into the microchannel reactor, $BF_3$ entered the microchannel reactor through the reaction gas header pipe, and the volume flow rate of $BF_3$ was 78 L/h, the volume flow rate of 1-nonene was 10 L/h, and the volume flow rate of isopropanol was 0.1 L/h. The polymerization reaction was performed in the microchannel reactor, the reaction temperature was 25° C., and the pressure was 4 MPa. The formed intermediate stream entered the high-pressure separator. The intermediate stream underwent the gas-liquid separation in the high-pressure separator. The separation temperature was 20° C. and the separation pressure was 4 MPa. The separated liquid phase was water-washed with the water washing device to obtain the polyolefin product. The $BF_3$ gas separated from the high-pressure separator were recycled by the compressor. The gas outlet pressure of the compressor was 4 MPa. The test results showed that the separation efficiency of the high-pressure separator was relatively low, and the recovery of the $BF_3$ gas was only 20%. After the system run stably, a small amount of polyolefin product sample in the high-pressure separator was taken, water washed, and measured by the gas chromatography for the content of each component in the product. The test results were as shown in Table 2.

TABLE 2

| Sample olefin composition distribution | Content |
| --- | --- |
| Monomer, % | 2.5 |
| Dimer, % | 7.9 |
| Trimer, % | 39.1 |
| Tetramer, % | 28.5 |
| Pentamer, % | 17.5 |
| ≥Hexamer, % | 4.5 |
| Conversion, % | 97.5 |

Comparative Example 2

The polymerization of the olefin raw material was carried out by using apparatus for preparing polyalpha-olefins shown in Example 1.

In the apparatus, the structure and parameter of the mixer was as follows: the allowable process fluid temperature range: 20-200° C., the upper limit of the working pressure (25° C.): 10 MPa; the structure and parameter of the microchannel reactor was as follows: 8 channels in parallel, the process fluid temperature range: −20 to 200° C., the maximum allowable reaction pressure: 6 MPa, the maximum allowable heat transfer medium pressure: 2 MPa, including two temperature probes for measuring the temperature in the reaction system, the fluid channel volume (without mixing disk): 50 mL, the reaction volume (in case of filling the mixing sheets) 30 mL, the volume flow rate: 3-30 L/h, with a header pipe for introducing the reaction gas and branch pipes for distributing the reaction gas to each channel; the high-pressure separator had a volume of 1 L, and a diameter of 10 cm; the low-pressure separator had a volume of 15 L and a diameter of 50 cm; the working parameter of the compressor was as follows, suction pressure: −0.1 to 0.03 MPa, exhaust pressure: 10 MPa, volumetric flow rate 3 m³/h; the back pressure valve had a pressure of 6 MPa; the dryer had an effective volume of 10 L, with a gas distributor at the bottom, silica gel filler disposed in the upper layer.

The mixed stream obtained by mixing 1-nonene and n-butanol in the mixer, and the $BF_3$ gas were each independently passed into the microchannel reactor, $BF_3$ entered the microchannel reactor through the reaction gas header pipe, and the volume flow rate of $BF_3$ was 26 L/h, the volume flow rate of 1-nonene was 10 L/h, and the volume flow rate of n-butanol was 0.1 L/h. The polymerization reaction was performed in the microchannel reactor, the reaction temperature was 20° C., and the pressure was 4 MPa. The formed intermediate stream entered the high-pressure separator. The intermediate stream underwent the first gas-liquid separation in the high-pressure separator. The separation temperature was 20° C. and the separation pressure was 4 MPa. The separated liquid phase entered the low-pressure separator for the second gas-liquid separation, the separation temperature was 20° C., and the separation pressure was 0.01 MPa. The liquid phase separated from the low-pressure separator was water-washed with the water washing device to obtain the polyolefin product. The $BF_3$ gases separated from the high-pressure separator and the low-pressure separator were recycled by the compressor. The gas outlet pressure of the compressor was 4 MPa. The $BF_3$ gas recovery was 40%. After the system run stably, a small amount of polyolefin product sample in the low-pressure separator was taken, water washed, and measured by the gas chromatography for the content of each component in the product. The test results were as shown in Table 3.

TABLE 3

| Sample olefin composition distribution | Content |
| --- | --- |
| Monomer, % | 36.7 |
| Dimer, % | 12.1 |
| Trimer, % | 25.2 |
| Tetramer, % | 17.8 |
| Pentamer, % | 5.1 |
| ≥Hexamer, % | 3.1 |
| Conversion, % | 63.3 |

Example 2

The polymerization of the olefin raw material was carried out by using the apparatus shown in FIG. 2.

In the apparatus used by the present Example, the mixing unit 1 was a mixer, the microchannel reaction unit 2 was a common microchannel reactor filled with mixing sheets (not the preferred microchannel reactor of the present invention), the high-pressure separation unit 3 was a high-pressure separator, the low-pressure separation unit 4 was a low-pressure separator, the gas circulation unit 5 was a compressor, the post-treatment unit 6 was a water washing device, the pressure control unit 7 was a back pressure valve, the gas purification unit 8 was a dryer.

In the apparatus, the structure and parameter of the mixer was as follows: the allowable process fluid temperature range: 20-200° C., the upper limit of the working pressure (25° C.): 10 MPa; the structure and parameter of the microchannel reactor was as follows: 8 channels in parallel, the process fluid temperature range: −20 to 200° C., the maximum allowable reaction pressure: 6 MPa, the maximum allowable heat transfer medium pressure: 2 MPa, including two temperature probes for measuring the temperature in the reaction system, the fluid channel volume (without mixing disk): 50 mL, the reaction volume (in case of filling the mixing sheets) 30 mL, the volume flow rate: 3-30 L/h, with a header pipe for introducing the reaction gas and branch pipes for distributing the reaction gas to each channel; the high-pressure separator had a volume of 1 L, and a diameter of 10 cm; the low-pressure separator had a volume of 15 L and a diameter of 50 cm; the working parameter of the compressor was as follows, suction pressure: −0.1 to 0.03 MPa, exhaust pressure: 10 MPa, volumetric flow rate 3 m³/h; the back pressure valve had a pressure of 6 MPa; the dryer was an adsorption dryer, had an effective volume of 10 L, with a gas distributor at the bottom, and silica gel filler disposed in the upper layer.

The mixed stream obtained by mixing 1-decene and n-butanol in the mixer, and the $BF_3$ gas were each independently passed into the microchannel reactor, $BF_3$ entered the microchannel reactor through the reaction gas header pipe, and the volume flow rate of $BF_3$ was 78 L/h, the volume flow rate of 1-decene was 10 L/h, and the volume flow rate of n-butanol was 0.1 L/h. The polymerization reaction was performed in the microchannel reactor, the reaction temperature was 20° C., and the pressure was 4 MPa. The formed intermediate stream entered the high-pressure separator. The intermediate stream underwent the first gas-liquid separation in the high-pressure separator. The separation temperature was 20° C. and the separation pressure was 4 MPa. The separated liquid phase entered the low-pressure separator for the second gas-liquid separation, the separation temperature was 20° C., and the separation pressure was 0.01 MPa. The liquid phase separated by the low-pressure separator was water-washed with the water washing device of the post-treatment unit 6 to obtain the final polyolefin product. The gas phases ($BF_3$ gases) separated from the high-pressure separator and the low-pressure separator were dried by the dryer and recycled by the compressor. The gas outlet pressure of the compressor was 4 MPa. After the system run stably, a small amount of polyolefin product sample in the low-pressure separator was taken, water washed, and measured by the gas chromatography for the content of each component in the product. The $BF_3$ gas recovery was 54%. The test results were as shown in Table 4.

TABLE 4

| Sample olefin composition distribution | Content |
|---|---|
| Monomer, % | 2.2 |
| Dimer, % | 6.1 |
| Trimer, % | 40.4 |
| Tetramer, % | 29.4 |
| Pentamer, % | 17.4 |
| ≥Hexamer, % | 4.5 |
| Conversion, % | 97.8 |

Example 3

The polymerization of the olefin raw material was carried out by using the apparatus shown in FIG. 3.

In the apparatus used by the present Example, the mixing unit 1 was a mixer, the microchannel reaction unit 2 was a common microchannel reactor filled with mixing sheets (not the preferred microchannel reactor of the present invention), the high-pressure separation unit 3 was a high-pressure separator, the low-pressure separation unit 4 was a low-pressure separator, the gas circulation unit 5 was a compressor, the post-treatment unit 6 was a sedimentation device, the pressure control unit 7 was a back pressure valve, and the gas purification unit 8 was a dryer; the mixer, the microchannel reactor, the high-pressure separator, the low-pressure separator, the compressor, and the dryer were identical to those of Example 1.

The sedimentation device did enable the separation of the stream entering therein into a light liquid phase and a heavy liquid phase, and the heavy liquid phase (containing the complex of auxiliary feed and $BF_3$, and the unreacted olefin raw material) was returned to the mixing unit 1 to continue the participation in the continuous reaction. The device was a horizontal gravitational sedimentation device, there was a cuboid container with a size of 3000 mm×300 mm×1500 mm inside the tank of said device, and there were coalescence inclined plates and flat plates inside said container, and ten flat plates were connected after every ten coalescence inclined plates. The spacing between the coalescence inclined plates was 30 mm, the inclination angle was 30°, and the length of the inclined plate is 34 mm. The flat plate had a length of 30 mm, and a spacing of 30 mm.

The mixed stream obtained by mixing 1-decene and n-butanol in the mixer, and the $BF_3$ gas were each independently passed into the microchannel reactor, $BF_3$ entered the microchannel reactor through the reaction gas header pipe, and the volume flow rate of $BF_3$ was 78 L/h, the volume flow rate of 1-decene was 10 L/h, and the volume flow rate of n-butanol was 0.1 L/h. The polymerization reaction was performed in the microchannel reactor, the reaction temperature was 20° C., and the pressure was 4 MPa. The formed intermediate stream entered the high-pressure separator. The intermediate stream underwent the first gas-liquid separation in the high-pressure separator. The separation temperature was 20° C. and the separation pressure was 4 MPa. The separated liquid phase entered the low-pressure separator for the second gas-liquid separation, the separation temperature was 20° C., and the separation pressure was 0.01 MPa. The liquid phase separated by the low-pressure separator entered the sedimentation device of the post-treatment unit 6, where the sedimentation separation occurred, and was divided into a light liquid phase and a heavy liquid phase. The light liquid phase was a crude polyolefin product, which was water washed to produce the final polyolefin product; the heavy liquid phase contained the complex of auxiliary feed and $BF_3$, and the unreacted olefin raw material, and was returned to the mixing unit 1. The gas phases separated from the high-pressure separator and the low-pressure separator were dried by the dryer, compressed by the compressor, and recycled for reuse. The gas outlet pressure of the compressor was 4 MPa. After the system run stably, a small amount of polyolefin product sample in the low-pressure separator was taken, water washed, and measured by the gas chromatography for the content of each component in the product. The recovery of the complex catalyst was 65%, and the $BF_3$ gas recovery was 75.45%. The test results were as shown in Table 5.

TABLE 5

| Sample olefin composition distribution | Content |
|---|---|
| Monomer, % | 2.9 |
| Dimer, % | 7.5 |
| Trimer, % | 39.1 |
| Tetramer, % | 28.6 |

TABLE 5-continued

| Sample olefin composition distribution | Content |
|---|---|
| Pentamer, % | 17.6 |
| ≥Hexamer, % | 4.3 |
| Conversion, % | 97.1 |

Example 4

The polymerization of the olefin raw material was carried out by using the apparatus for preparing polyolefins as shown in FIG. 3.

In the apparatus used by the present Example, the mixing unit 1 was a mixer, the microchannel reaction unit 2 was a common microchannel reactor filled with mixing sheets (not the preferred microchannel reactor of the present invention), the high-pressure separation unit 3 was a high-pressure separator, the low-pressure separation unit 4 was a low-pressure separator, the gas circulation unit 5 was a compressor, the post-treatment unit 6 was a centrifugation device, the pressure control unit 7 was a back pressure valve, the gas purification unit 8 was a dryer, the dryer had an effective volume of 10 L with a gas distributor at the bottom and silica gel filler disposed in the upper layer; wherein the mixer, the microchannel reactor, the high-pressure separator, the low-pressure separator, and the compressor were identical to those of Example 1.

The centrifugation device did enable the separation of the stream entering therein into a light liquid phase and a heavy liquid phase, and the heavy liquid phase (containing the complex of auxiliary feed and $BF_3$, and the unreacted olefin raw material) was returned to the mixing unit 1 to continue the participation in the continuous reaction.

Among others, the centrifugation device was a tubular high-speed separator, the rotation speed of the rotating drum was 10-30000 r/min, the separation degree was not less than 15000 G; the centrifugation separation temperature was 10-60° C., and the centrifugation residence time was 10-1000s.

The mixed stream obtained by mixing 1-decene and n-butanol in the mixer, and the $BF_3$ gas were each independently passed into the microchannel reactor, $BF_3$ entered the microchannel reactor through the reaction gas header pipe, and the volume flow rate of $BF_3$ was 78 L/h, the volume flow rate of 1-decene was 10 L/h, and the volume flow rate of n-butanol was 0.1 L/h. The polymerization reaction was performed in the microchannel reactor, the reaction temperature was 20° C., and the pressure was 4 MPa. The formed intermediate stream entered the high-pressure separator. The intermediate stream underwent the first gas-liquid separation in the high-pressure separator. The separation temperature was 20° C. and the separation pressure was 4 MPa. The separated liquid phase entered the low-pressure separator for the second gas-liquid separation, the separation temperature was 20° C., and the separation pressure was-0.01 MPa. The liquid phase separated by the low-pressure separator entered the centrifugation device of the post-treatment unit 6. In the centrifugation device, the separated light liquid phase was a crude polyolefin product, which was water washed to produce the final polyolefin product; the separated heavy liquid phase contained the complex of auxiliary feed and $BF_3$, and the unreacted olefin raw material, and was returned to the mixing unit 1 to continue the participation in the continuous reaction. The gas phases (the $BF_3$ gas) separated from the high-pressure separator and the low-pressure separator were dried by the dryer, compressed by the compressor, and recycled for reuse. The gas outlet pressure of the compressor was 4 MPa. After the system run stably, a small amount of polyolefin product sample in the low-pressure separator was taken, water washed, and measured by the gas chromatography for the content of each component in the product. The recovery of the complex catalyst was 80%. The total recovery of the $BF_3$ gas was 80.4%. The test results were as shown in Table 6.

TABLE 6

| Sample olefin composition distribution | Content |
|---|---|
| Monomer, % | 2.1 |
| Dimer, % | 7.3 |
| Trimer, % | 39.4 |
| Tetramer, % | 29.0 |
| Pentamer, % | 17.6 |
| ≥Hexamer, % | 4.6 |
| Conversion, % | 97.9 |

Comparative Example 3

The polymerization of the olefin raw material was carried out by only using the mixers, the microchannel reactor, and the centrifugation device that are identical to those used in the apparatus for preparing polyalpha-olefins in Example 4.

The mixed stream obtained by mixing 1-decene and n-butanol in the mixer, and the $BF_3$ gas were passed into the microchannel reactor, $BF_3$ entered the microchannel reactor through the reaction gas header pipe, and the volume flow rate of $BF_3$ was 78 L/h, the volume flow rate of 1-decene was 10 L/h, and the volume flow rate of n-butanol was 0.1 L/h. The polymerization reaction was performed in the microchannel reactor, the reaction temperature was 20° C., and the pressure was 4 MPa. The intermediate product from the microchannel reactor directly enters the centrifugation device, and the $BF_3$ gas is not recovered. In the centrifugation device, the separated light liquid phase was a crude polyolefin product, which was water washed to produce the final polyolefin product; the separated heavy liquid phase contained the complex of auxiliary feed and $BF_3$, and the unreacted olefin raw material, and was returned to the mixing unit 1 to continue the participation in the continuous reaction. The recovery of the complex catalyst was 80%. The total recovery of the $BF_3$ gas was 26.4%. A small amount of polyolefin product sample was taken, and measured by the gas chromatography for the content of each component in the product. The test results were as shown in Table 7.

TABLE 7

| Sample olefin composition distribution | Content |
|---|---|
| Monomer, % | 3.4 |
| Dimer, % | 8.0 |
| Trimer, % | 39.1 |
| Tetramer, % | 28.2 |
| Pentamer, % | 17.0 |
| ≥Hexamer, % | 4.3 |
| Conversion, % | 96.8 |

Example 5

The polymerization of the olefin raw material was carried out by using the apparatus for preparing polyolefins as shown in FIG. 2.

In the apparatus, the mixing unit 1 was a mixer, the microchannel reaction unit 2 was a preferred microchannel reactor (the preferred microchannel reactor of the present invention) as shown in FIG. 4, the high-pressure separation unit 3 was a high-pressure separator, the low-pressure separation unit 4 was a low-pressure separator, the gas circulation unit 5 was a compressor, the post-treatment unit 6 was a water washing device, the pressure control unit 7 was a back pressure valve, and the gas purification unit 8 was a dryer, wherein the mixer, the high-pressure separator, the low-pressure separator, and the compressor were identical to those of Example 1.

Figures 6, 7:
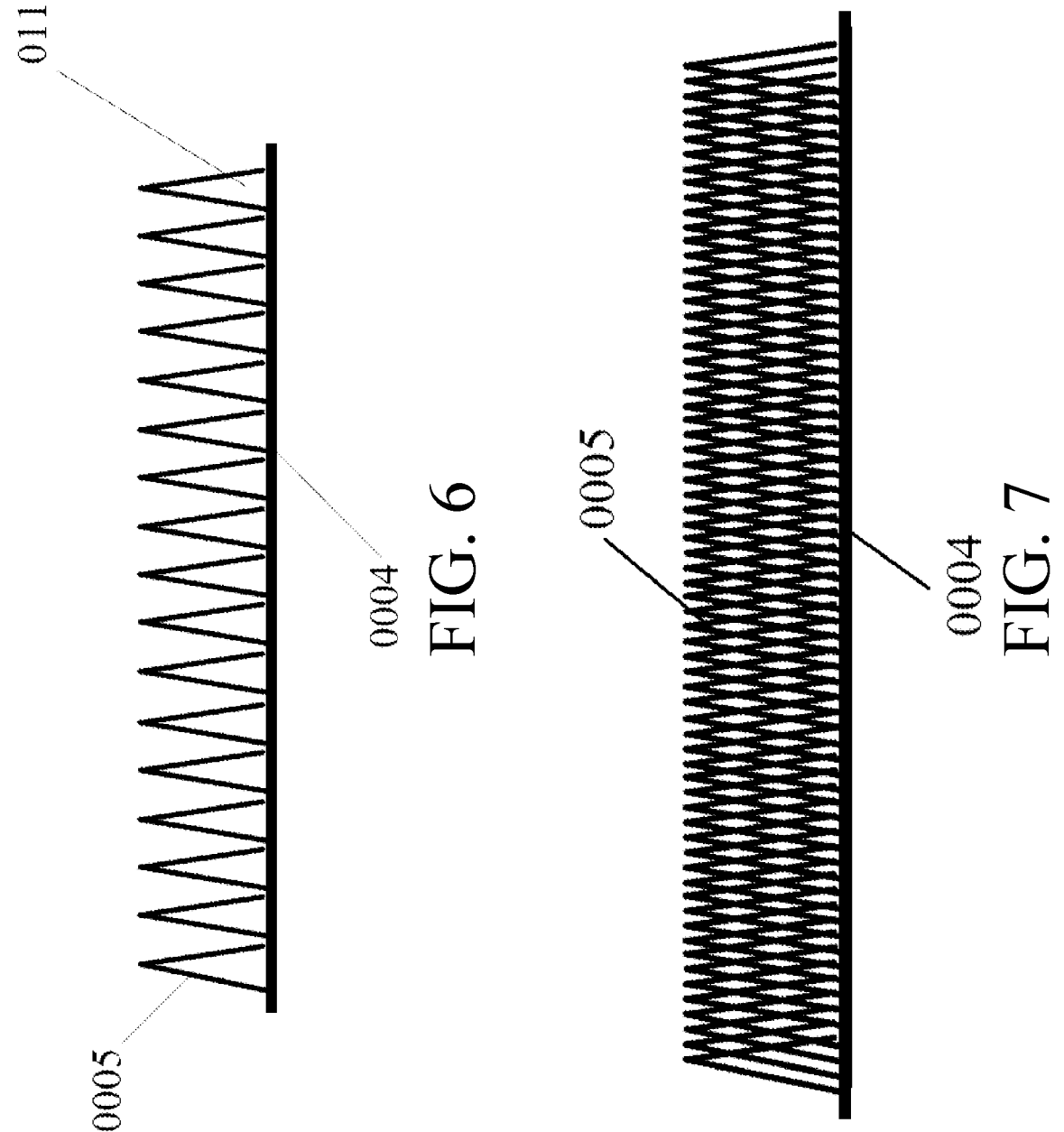
FIG. 6 is a structural representation of the second mixing member according to the embodiment of the present invention.
FIG. 7 is a structural representation for superimposing a plurality of the second mixing members according to the embodiment of the present invention.

In the apparatus, The microchannel reactor contained 5 reaction channels 010 in parallel, each reaction channel 010 had a rectangular cross-section with a cross-sectional area of 20 mm$^2$, and the reaction channel 010 had a length of 2000 mm. The second mixing member 011 in the reaction channel 010 had triangular tooth elements 0005, and the spacing between adjacent tooth elements 0005 was 5 mm. In the reaction channel 010, a total of four layers of superimposed second mixing members 011 as shown in FIG. 7 were arranged. In the apparatus, the high-pressure separator had a volume of 1 L, and a diameter of 10 cm; the low-pressure separator had a volume of 15 L and a diameter of 50 cm; the compressor had a suction pressure of −0.1 to 0.03 MPa, an exhaust pressure of MPa, and a volumetric flow rate of 3 m$^3$/h; the back pressure valve had a pressure of 6 MPa; the dryer had an effective volume of 10 L, with a gas distributor at the bottom, and silica gel filler disposed in the upper layer.

Into the microchannel reactor were passed, the mixed stream obtained by mixing 1-decene and n-butanol in the mixer, through the feed pipe 002, and the BF$_3$ gas, through the fluid distribution pipe 017; the volume flow rate of BF$_3$ was 78 L/h, the volume flow rate of decene was 10 L/h, and the volume flow rate of n-butanol was 0.1 L/h. The polymerization reaction was performed in the microchannel reactor, the reaction temperature was 20° C., and the pressure was 4 MPa. The BF$_3$ gas separated from the high-pressure separator and the low-pressure separator was dried by the dryer, compressed by the compressor, and recycled for reuse. The gas outlet pressure of the compressor was 4 MPa. The BF$_3$ gas recovery was 54%. After the system run stably, a small amount of polyolefin product sample in the low-pressure separator was taken, water washed, and measured by the gas chromatography for the content of each component in the product. The test results were as shown in Table 8.

TABLE 8

| Sample olefin composition distribution | Content |
| --- | --- |
| Monomer, % | 0.3 |
| Dimer, % | 2.7 |
| Trimer, % | 43.0 |
| Tetramer, % | 31.5 |
| Pentamer, % | 18.1 |
| ≥Hexamer, % | 4.4 |
| Conversion, % | 99.7 |

Comparative Example 4

The polymerization of the olefin raw material was carried out by using the apparatus for preparing polyolefins as shown in FIG. 2.

In the apparatus, the mixing unit 1 was a mixer, the microchannel reaction unit 2 was a preferred microchannel reactor (the preferred microchannel reactor of the present invention) as shown in FIG. 4, but the reactor was not provided with the mixing channel 014 and the fluid distributor 016, the high-pressure separation unit 3 was a high-pressure separator, the low-pressure separation unit 4 was a low-pressure separator, the gas circulation unit 5 was a compressor, the post-treatment unit 6 was a water washing device, the pressure control unit 7 was a back pressure valve, the gas purification unit 8 was a dryer, wherein the mixer, the high-pressure separator, the low-pressure separator, and the compressor were identical to those of Example 1.

In the apparatus, the microchannel reactor contained 5 reaction channels 010 in parallel, each reaction channel 010 had a rectangular cross-section with a cross-sectional area of 20 mm$^2$, and the reaction channel 010 had a length of 2000 mm. The second mixing member 011 in the reaction channel 010 had triangular tooth elements 0005, and the spacing between adjacent tooth elements 0005 was 5 mm. In the reaction channel 010, a total of four layers of superimposed second mixing members 011 as shown in FIG. 7 were arranged.

In the apparatus, the high-pressure separator had a volume of 1 L, and a diameter of 10 cm; the low-pressure separator had a volume of 15 L and a diameter of 50 cm; the compressor had a suction pressure of −0.1 to 0.03 MPa, an exhaust pressure of 10 MPa, and a volumetric flow rate of 3 m$^3$/h; the back pressure valve had a pressure of 6 MPa; the dryer had an effective volume of 10 L, with a gas distributor at the bottom, and silica gel filler disposed in the upper layer.

Into the microchannel reactor were passed, the mixed stream obtained by mixing 1-decene and n-butanol in the mixer, through the feed pipe 002, and the BF$_3$ gas, through the fluid distribution pipe 017; the volume flow of BF$_3$ was 78 L/h, the volume flow rate of decene was 10 L/h, and the volume flow rate of n-butanol was 0.1 L/h. The polymerization reaction was performed in the microchannel reactor, the reaction temperature was 20° C., and the pressure was 4 MPa. The BF$_3$ gas separated from the high-pressure separator and the low-pressure separator was dried by the dryer, compressed by the compressor, and recycled for reuse. The gas outlet pressure of the compressor was 4 MPa. The BF$_3$ gas recovery was 58%. After the system run stably, a small amount of polyolefin product sample in the low-pressure separator was taken, water washed, and measured by the gas chromatography for the content of each component in the product. The test results were as shown in Table 9.

TABLE 9

| Sample olefin composition distribution | Content |
| --- | --- |
| Monomer, % | 19.4 |
| Dimer, % | 13.2 |
| Trimer, % | 23.9 |
| Tetramer, % | 23.4 |
| Pentamer, % | 14.5 |
| ≥Hexamer, % | 5.6 |
| Conversion, % | 80.6 |

Example 6

The polymerization of the olefin raw material was carried out by using the apparatus for preparing polyolefins as shown in FIG. 2.

In the apparatus, the mixing unit 1 was a mixer, the microchannel reaction unit 2 was a preferred microchannel reactor (the preferred microchannel reactor of the present invention) as shown in FIG. 4, the high-pressure separation unit 3 was a high-pressure separator, the low-pressure separation unit 4 was a low-pressure separator, the gas circulation unit 5 was a compressor, the post-treatment unit 6 was a water washing device, the pressure control unit 7 was a back pressure valve, the gas purification unit 8 was a dryer, wherein the mixer, the high-pressure separator, the low-pressure separator, and the compressor were identical to those of Example 1.

In the apparatus, the microchannel reactor contained 5 reaction channels 010 in parallel, each reaction channel 010 had a rectangular cross-section with a cross-sectional area of 20 mm², and the reaction channel 010 had a length of 2000 mm. The second mixing member 011 in the reaction channel 010 had triangular tooth elements 0005, and the spacing between adjacent tooth elements 0005 was 5 mm. In the reaction channel 010, a total of four layers of superimposed second mixing members 011 as shown in FIG. 7 were arranged. The reactor contained one mixing channel 014, which had a cross-sectional area of 10 cm2 and a length of 800 mm. The fluid distributor 016 was a metal powder sintered body with micropores having an average pore size of 5 microns, a cross-sectional area of 8.5 cm2 and a length of 150 mm. Three first mixing members 015 were provided in the mixing channel 014.

In the apparatus, the high-pressure separator had a volume of 1 L, and a diameter of 10 cm; the low-pressure separator had a volume of 15 L and a diameter of 50 cm; the compressor had a suction pressure of –0.1 to 0.03 MPa, an exhaust pressure of 10 MPa, and a volumetric flow rate of 3 m³/h; the back pressure valve had a pressure of 6 MPa; the dryer had an effective volume of 10 L, with a gas distributor at the bottom, and silica gel filler disposed in the upper layer.

Into the microchannel reactor were passed, the mixed stream obtained by mixing 1-decene and n-butanol in the mixer, through the feed pipe 002, and the BF₃ gas, through the fluid distribution pipe 017; the volume flow of BF₃ was 78 L/h, the volume flow rate of decene was 10 L/h, and the volume flow rate of n-butanol was 0.1 L/h. The polymerization reaction was performed in the microchannel reactor, the reaction temperature was 20° C., and the pressure was 4 MPa. The BF₃ gas separated from the high-pressure separator and the low-pressure separator was dried by the dryer, compressed by the compressor, and recycled for reuse. The gas outlet pressure of the compressor was 4 MPa. The BF₃ gas recovery was 55%. After the system run stably, a small amount of polyolefin product sample in the low-pressure separator was taken, water washed, and measured by the gas chromatography for the content of each component in the product. The test results were as shown in Table 10.

TABLE 10

| Sample olefin composition distribution | Content |
| --- | --- |
| Monomer, % | 4.9 |
| Dimer, % | 10.5 |
| Trimer, % | 38.2 |
| Tetramer, % | 27.5 |
| Pentamer, % | 15.7 |
| ≥Hexamer, % | 3.2 |
| Conversion, % | 95.1 |

Example 7

The polymerization of the olefin raw material was carried out by using the apparatus for preparing polyolefins as shown in FIG. 2.

In the apparatus, the mixing unit 1 was a mixer, the microchannel reaction unit 2 was a preferred microchannel reactor (the preferred microchannel reactor of the present invention) as shown in FIG. 4, the high-pressure separation unit 3 was a high-pressure separator, the low-pressure separation unit 4 was a low-pressure separator, the gas circulation unit 5 was a compressor, the post-treatment unit 6 was a water washing device, the pressure control unit 7 was a back pressure valve, the gas purification unit 8 was a dryer, wherein the mixer, the high-pressure separator, the low-pressure separator, and the compressor were identical to those of Example 1.

In the apparatus, the microchannel reactor contained 5 reaction channels 010 in parallel, each reaction channel 010 had a rectangular cross-section with a cross-sectional area of 20 mm², and the reaction channel 010 had a length of 2000 mm. The second mixing member 011 in the reaction channel 010 had triangular tooth elements 0005, and the spacing between adjacent tooth elements 0005 was 5 mm. In the reaction channel 010, a total of four layers of superimposed second mixing members 011 as shown in FIG. 7 were arranged. The reactor contained two mixing channels 014, each of which had a cross-sectional area of 10 cm2 and a length of 800 mm. Three first mixing members 015 were provided in each mixing channel 014. The fluid distributor 016 was made of micro/mesoporous tube material, and the hollow microchannels constituting the network framework of the micro/mesoporous tube material had a cross-sectional area of 8.5 cm2, an average pore diameter of 2 microns, and a length of 150 mm.

In the apparatus, the high-pressure separator had a volume of 1 L, and a diameter of 10 cm; the low-pressure separator had a volume of 15 L and a diameter of 50 cm; the compressor had a suction pressure of 0.1 to 0.03 MPa, an exhaust pressure of 10 MPa, and a volumetric flow rate of 3 m³/h; the back pressure valve had a pressure of 6 MPa; the dryer had an effective volume of 10 L, with a gas distributor at the bottom, and silica gel filler disposed in the upper layer.

Into the microchannel reactor were passed, the mixed stream obtained by mixing 1-decene and n-butanol in the mixer, through the feed pipe 002, and the BF₃ gas, through the fluid distribution pipe 017; the volume flow of BF₃ was 78 L/h, the volume flow rate of decene was 10 L/h, and the volume flow rate of n-butanol was 0.1 L/h. The polymerization reaction was performed in the microchannel reactor, the reaction temperature was 20° C., and the pressure was 4 MPa. The BF₃ gas separated from the high-pressure separator and the low-pressure separator was dried by the dryer, compressed by the compressor, and recycled for reuse. The gas outlet pressure of the compressor was 4 MPa. The BF₃ gas recovery was 54%. After the system run stably, a small amount of polyolefin product sample in the low-pressure separator was taken, water washed, and measured by the gas chromatography for the content of each component in the product. The test results were as shown in Table 11.

TABLE 11

| Sample olefin composition distribution | Content |
| --- | --- |
| Monomer, % | 0.4 |
| Dimer, % | 2.8 |
| Trimer, % | 43.0 |
| Tetramer, % | 31.4 |
| Pentamer, % | 15.6 |
| ≥Hexamer, % | 6.8 |
| Conversion, % | 99.6 |

Comparative Example 5

The same apparatus as Example 2 was used except that no mixing sheet was filled in the microchannel reactor.

The mixed stream obtained by mixing 1-decene and n-butanol in the mixer, and the $BF_3$ gas were each independently passed into the microchannel reactor, $BF_3$ entered the microchannel reactor through the reaction gas header pipe, and the volume flow rate of $BF_3$ was 78 L/h, the volume flow rate of 1-decene was 10 L/h, and the volume flow rate of n-butanol was 0.1 L/h. The polymerization reaction was performed in the microchannel reactor, the reaction temperature was 20° C., and the pressure was 4 MPa. The formed intermediate stream entered the high-pressure separator. The intermediate stream underwent the first gas-liquid separation in the high-pressure separator. The separation temperature was 20° C. and the separation pressure was 4 MPa. The separated liquid phase entered the low-pressure separator for the second gas-liquid separation, the separation temperature was 20° C., and the separation pressure was 0.01 MPa. The liquid phase separated by the low-pressure separator was water-washed with the water washing device of the post-treatment unit 6 to obtain the final polyolefin product. The gas phases ($BF_3$ gases) separated from the high-pressure separator and the low-pressure separator were dried by the dryer and recycled by the compressor. The gas outlet pressure of the compressor was 4 MPa. After the system run stably, a small amount of polyolefin product sample in the low-pressure separator was taken, water washed, and measured by the gas chromatography for the content of each component in the product. The $BF_3$ gas recovery was 53%. The test results were as shown in Table 12.

TABLE 12

| Sample olefin composition distribution | Content |
| --- | --- |
| Monomer, % | 21.9 |
| Dimer, % | 6.1 |
| Trimer, % | 25.3 |
| Tetramer, % | 22.5 |
| Pentamer, % | 14.9 |
| ≥Hexamer, % | 9.3 |
| Conversion, % | 78.1 |

The polyolefin products of Example 1-7 and Comparative Example 1-5 were distilled and cut respectively to obtain polyalpha-olefin synthetic oils above 280° C., and the kinematic viscosity at 100° C. and the viscosity index were tested. The test results were shown in Table 13.

TABLE 13

| Performance evaluation | Kinematic viscosity at 100° C., mm²/s | Viscosity index |
| --- | --- | --- |
| Example 1 | 5.245 | 145 |
| Comparative Example 1 | 5.212 | 140 |
| Comparative Example 2 | 3.673 | 126 |
| Example 2 | 5.247 | 145 |
| Example 3 | 5.244 | 145 |
| Example 4 | 5.249 | 146 |
| Comparative Example 3 | 5.139 | 139 |
| Example 5 | 5.711 | 147 |
| Comparative Example 4 | 4.295 | 131 |
| Example 6 | 4.769 | 136 |
| Example 7 | 5.603 | 145 |
| Comparative Example 5 | 4.612 | 134 |

It can be seen from the above examples that the apparatus for preparing polyalpha-olefins of the present invention could recover $BF_3$ and $BF_3$ complexes with high recovery, thereby avoiding environmental pollution and further reducing the reaction cost.

In addition, as can be seen from the above table, by using the preferred microchannel reactor of the present invention, the polyalpha-olefin synthetic oil could be obtained at a high conversion. This is because the reaction channel 010 and the mixing channel 014 are both tubular structures arranged in the same direction, so that the mixed fluid can form a stable plug flow along the first direction, improving the consistency of the residence time of the mixed fluid, and avoiding or reducing the formation of the undesired products. In addition, the reaction channel 010 is provided with a second mixing member 011, and the mixing channel 014 is provided with a fluid distributor 016 and a first mixing member 015, which can further improve the turbulence degree of the mixed fluid, improve the uniformity of mixing, and further avoid or reduce the production of undesired products, and improve the conversion of the target product. Moreover, the resulting polyalpha-olefin synthetic oils had low kinematic viscosity and high viscosity index.

The preferred embodiments of the present invention have been described above in detail with reference to the accompanying drawings, however, the present invention is not limited thereto. Within the scope of the technical concept of the present invention, various simple modifications can be made to the technical solutions of the present invention, including the combinations of various specific technical features in any suitable manner. These simple modifications and combinations should also be regarded as the disclosed content of the present invention, and all belong to the protection scope of the present invention.

The invention claimed is:

1. A process for preparing polyalpha-olefin synthetic base oils in a reaction apparatus comprising a mixing unit, a microchannel reaction unit comprising a plurality of microchannel reactors, a high-pressure separation unit, a low-pressure separation unit, a post-treatment unit, and a gas circulation unit that are fluidly connected, comprising:

S1: forming a mixed stream comprising an olefin raw material and an auxiliary feed in the mixing unit;

S2: mixing the mixed stream and a $BF_3$ gas in a plurality of mixing channels in a mixing zone of each microchannel reactor to form a reactant mixture, wherein a number of the plurality of mixing channels is 2-10;

S3: introducing the reactant mixture into a reaction zone of each microchannel reactor, wherein the olefine raw material undergoes polymerization in a plurality of reaction channels in the reaction zone of each microchannel reactor to form an intermediate stream, wherein a number of the plurality of the reaction channels ranges from 2 to 500;

S4: feeding the intermediate stream into the high-pressure separation unit, in which the intermediate stream undergoes a first gas-liquid separation to form a first liquid phase and a first gas phase;

S5: feeding the first liquid phase into a low-pressure separation unit, in which the first liquid phase undergoes a second gas-liquid separation to form a second liquid phase and a second gas phase;

S6: feeding the second liquid phase into a post-treatment unit for a post-treatment to obtain a polyolefin product; and S7: feeding the first and the second gas phases comprising $BF_3$ into a gas circulation unit to be recycled, wherein a recycled $BF_3$ is a portion of the $BF_3$ being fed into the microchannel reactor, wherein the post-treatment is one or more selected from adsorption, extraction, distillation, centrifugation, sedimentation, alkaline washing, and water washing, and wherein, in S2, each of the plurality of mixing channels has an inlet adapted to receive the mixed stream and an outlet fluidly connected to the reaction zone, wherein the $BF_3$ gas is introduced into the plurality of mixing channels in each microchannel reactor through a fluid distribution pipe having a plurality of branch pipes, each branch pipe has one or more fluid distributors and extends into one of the plurality of mixing channels through the inlet thereof so that the $BF_3$ gas is introduced into the mixed stream inside each mixing channel through the one or more fluid distributors.

2. The process according to claim 1, wherein the olefin raw material comprises one or more of $C_3$-$C_{20}$ alpha-olefins; and/or, the auxiliary feed is selected from one or more of an alcohol having a carbon atom number of 1-20, an ether having a carbon atom number of 1-20, an aldehyde having a carbon atom number of 1-20, a ketone having a carbon atom number of 1-20, an ester having a carbon atom number of 1-30, a carboxylic acid having a carbon atom number of 1-20, and a phenol having a carbon atom number of 1-20.

3. The process according to claim 1, wherein the olefin raw material enters the mixing unit at a rate of 10-5000 L/h, the auxiliary feed enters the mixing unit at a rate of 0.01-1000 L/h, the $BF_3$ gas enters the microchannel reaction unit at a rate of 5-200000 L/h.

4. The process according to claim 1, wherein a reaction temperature in each microchannel reactor operates at a temperature of 0-120° C. at a reaction pressure of 0.01-10 MPa, a residence time of the olefin raw material in each microchannel reactor is 1-3600 seconds, and in each microchannel reactor, a mass ratio of the auxiliary feed:the olefin raw material:$BF_3$ is 1:1-1000:1-500.

5. The process according to claim 1, wherein the high-pressure separation unit is a high-pressure separator operating at a pressure of 0.01-10 MPa and a temperature of 0-120° C., and having a volume of 0.1-20000 L; and/or, the low-pressure separation unit is a low-pressure separator operating at a pressure of –0.1 to 1 MPa, at a temperature of 0-120° C., and has a volume of 0.1-20000 L; and/or, a pressure of the recycled $BF_3$ gas through the gas circulation unit is 0.01-10 MPa.

6. The process according to claim 1, wherein the post-treatment method is sedimentation or centrifugation, the sedimentation or centrifugation enables the separation of the stream entering the post-treatment unit into a light liquid phase and a heavy liquid phase containing the complex of the auxiliary feed and $BF_3$ and the unreacted olefin raw material obtained after the treatment in the post-treatment unit, wherein the process further comprises S7: feeding the heavy liquid phase to the mixing unit.

7. The process according to claim 1, wherein S7 further comprises drying and/or purifying the first and the second gas phases in a gas purification unit prior to entering the gas circulation unit, and the gas purification unit is one or more of a gas filter, an adsorption dryer, a freeze dryer, and a cyclone separator.

8. The process according to claim 1, wherein S1 further comprises feeding the $BF_3$ gas into the mixing unit at a rate of 4-180000 L/h.

9. The process according to claim 8, wherein S7 comprises feeding the first and the second gas phases into the mixing unit.

10. The process according to claim 8, wherein, based on a total mass of the $BF_3$ in the microchannel reaction unit, the mass ratio of $BF_3$ fed into the microchannel reaction unit to $BF_3$ fed in the mixing unit is 100-10:0-90.

11. The process according to claim 10, wherein based on the total mass of the $BF_3$ in the microchannel reaction unit, the mass ratio of the $BF_3$ gas that directly enters the microchannel reaction unit to the $BF_3$ gas that is mixed in the mixing unit is 100-10:0-90, in the case of feeding the $BF_3$ gas to the mixing unit, the $BF_3$ gas and the auxiliary feed are mixed to form a complex, and then mixed with the olefin raw material; or the auxiliary feed and the olefin raw material are mixed, and then mixed with the $BF_3$ gas; or the $BF_3$ gas, the olefin raw material and the auxiliary feed are mixed concurrently.

12. The process according to claim 1, wherein each fluid distributor is a cylindrical powder sintered body with micropores, and/or the fluid distributor has a cross-sectional area of 0.01 $cm^2$-200 $cm^2$, and a length of 1 mm-2000 m; and/or, the mixing channel has a cross-sectional area of 0.05 $cm^2$-400 $cm^2$, and a length of 50 mm-5000 mm; and/or the mixing zone comprises a first heat exchange cavity disposed in a shell of each microchannel reactor, the mixing channel is disposed in the first heat exchange cavity, the volumetric ratio of the first heat exchange cavity to the mixing channel is 5-30; and/or the reaction zone is provided with 2-500 parallel reaction channels extending along the first direction and communicated with the mixing channel via a transition zone of each microchannel reactor; and/or, the reaction channel is provided with a second mixing member, and the second mixing member includes a base strip extending along the first direction and a tooth element connected to the base strip and extended transversely to the base strip, the tooth element is of triangular shape, and on one side of the triangle adjacent to the base strip, one corner is connected to the base strip, and the other corner is 0.01 mm-20 mm away from the base strip; and/or the cross-section of the reaction channel is rectangular, and the tooth elements extend between a set of opposite sides of the rectangle; and/or the reaction channel has a cross-sectional area of 1 $mm^2$-150 $mm^2$, and a length of 100 mm-3000 mm, the minimum distance between the reaction channels is 3 mm-30 mm, and the second mixing member has a thickness of 0.2 mm-2 mm, and the spacing between adjacent tooth elements is 1.5 mm-20 mm; and/or, the reaction zone is provided with a second heat exchange cavity disposed in a shell of each microchannel reactor, the reaction channel is disposed in the second heat exchange cavity, the volumetric ratio of the second heat exchange cavity to the reaction channel is 5-30.

13. The process according to claim 1, wherein the rate for the olefin raw material entering the mixing unit is 40-2500 L/h, the rate for the auxiliary feed entering the mixing unit is 0.2-500 L/h, the gas-entering rate for the $BF_3$ gas entering the microchannel reaction unit is 100-50000 L/h; and/or reaction temperature in the microchannel reaction unit is 20-60° C., the reaction pressure in the microchannel reaction unit is 0.1-6 MPa; and/or the residence time of the olefin raw material in the microchannel reaction unit is 15-1000 seconds; and/or in the microchannel reaction unit, the mass ratio of the auxiliary feed:the olefin raw material:the total amount of $BF_3$ gas is 1:10-250:1.5-100; and/or the high-pressure separation unit is a high-pressure separator, the pressure of the high-pressure separator is 0.1-6 MPa, the temperature of the high-pressure separator is 20-60° C., the volume of the high-pressure separator is 0.2-2000 L; and/or, the low-pressure separation unit is a low-pressure separator, the pressure of the low-pressure separator is-0.1 to 0.1 MPa, the temperature of the low-pressure separator is 20-60° C., the volume of the low-pressure separator is 0.2-2000 L; and/or, the pressure of the recycled $BF_3$ gas through the gas circulation unit is 0.1-6 MPa; and/or, the pressure of the pressure control unit is 0.1-6 MPa; and/or, besides the olefin raw material and the auxiliary feed, the $BF_3$ gas is further mixed, and the rate for the $BF_3$ gas entering the mixing unit is 90-45000 L/h.

\* \* \* \* \*